United States Patent
Ohta et al.

(10) Patent No.: US 7,973,145 B2
(45) Date of Patent: *Jul. 5, 2011

(54) SULFONATED SUGAR COMPOUNDS, PHARMACEUTICAL COMPOSITIONS WHICH CONTAIN THE SAME, AND METHODS OF TREATING TUMORS WITH THE SAME

(75) Inventors: Keisuke Ohta, Nagareyama (JP); Masahiko Miura, Matsudo (JP); Kengo Sakaguchi, Tsukuba (JP); Fumio Sugawara, Niiza (JP); Noriyuki Sato, Sapporo (JP); Hiroeki Sahara, Sagamihara (JP); Nobuaki Takahashi, Rishiri-gun (JP); Yoko Mori, Ushiku (JP); Takayuki Yamazaki, Yokohama (JP); Kazuyoshi Masaki, Sakado (JP); Hiroshi Murata, Noda (JP)

(73) Assignee: Toyo Suisan Kaisha, Ltd., Tokyo (JP)

( * ) Notice: Subject to any disclaimer, the term of this patent is extended or adjusted under 35 U.S.C. 154(b) by 112 days.

This patent is subject to a terminal disclaimer.

(21) Appl. No.: 12/322,151

(22) Filed: Jan. 29, 2009

(65) Prior Publication Data

US 2009/0209475 A1  Aug. 20, 2009

Related U.S. Application Data

(63) Continuation of application No. PCT/JP2008/063056, filed on Jul. 18, 2008.

(30) Foreign Application Priority Data

Jul. 20, 2007  (JP) .................................. 2007-190120

(51) Int. Cl.
C07G 3/00 (2006.01)
C07H 11/00 (2006.01)
C07H 15/00 (2006.01)
C07H 17/00 (2006.01)
C07H 1/00 (2006.01)
A01N 43/04 (2006.01)
A61K 31/70 (2006.01)

(52) U.S. Cl. ........................... 536/4.1; 536/1.11; 514/25
(58) Field of Classification Search .................. 536/4.1, 536/1.11; 514/25
See application file for complete search history.

(56) References Cited

U.S. PATENT DOCUMENTS

| | | | |
|---|---|---|---|
| 6,395,886 B1 | 5/2002 | Yamazaki et al. | |
| 6,444,795 B1 | 9/2002 | Yamazaki et al. | |
| 6,518,248 B1 * | 2/2003 | Yamazaki et al. | 514/25 |
| 6,518,410 B2 * | 2/2003 | Yamazaki et al. | 536/4.1 |
| 6,670,361 B2 * | 12/2003 | Yamazaki et al. | 514/250 |
| 6,770,629 B2 * | 8/2004 | Yamazaki et al. | 514/25 |
| 7,148,200 B2 * | 12/2006 | Yamazaki et al. | 514/25 |
| 7,378,398 B2 * | 5/2008 | Yamazaki et al. | 514/25 |
| 2002/0028776 A1 | 3/2002 | Yamazaki et al. | |
| 2006/0252703 A1 | 11/2006 | Yamazaki et al. | |
| 2007/0219145 A1 | 9/2007 | Sakimoto et al. | |

FOREIGN PATENT DOCUMENTS

| | | |
|---|---|---|
| CA | 2064772 A1 | 2/1991 |
| JP | 5-501105 A | 3/1993 |
| JP | 11-106395 A | 4/1999 |
| JP | 2000-143516 A | 5/2000 |
| JP | 2002-338474 A | 11/2002 |
| JP | 2004-256656 A | 9/2004 |
| WO | WO 00/51622 A1 | 9/2000 |
| WO | WO 2006/001374 A1 | 1/2006 |

OTHER PUBLICATIONS

Sahara, H. et al. (2002) Anti-tumor Effect of Chemically Synthesized Sulfolipids Based on Sea Urchin's Natural Sulfonoquinovosylmonoacylglycerols. Japanese Journal of Cancer Research, vol. 93, p. 85-92.*
Eric J. Hall, "Radiosensitizers and Bioreductive Drugs," *Radiobiology for the Radiologist*, Fourth Edition, (1995), pp. 165-181.
English-language International Preliminary Report on Patentability and Written Opinion of the International Searching Authority dated Feb. 18, 2010 for International Application PCT/JP2008/063056 filed Jul. 18, 2008; Applicants: Toyo Suisan Kaisha, Ltd. et al.

* cited by examiner

*Primary Examiner* — Anna Jiang
*Assistant Examiner* — Scarlett Goon
(74) *Attorney, Agent, or Firm* — Holtz, Holtz, Goodman & Chick, PC

(57) ABSTRACT

Sulfoquinovosylacyl propanediol compounds represented by formula (I):

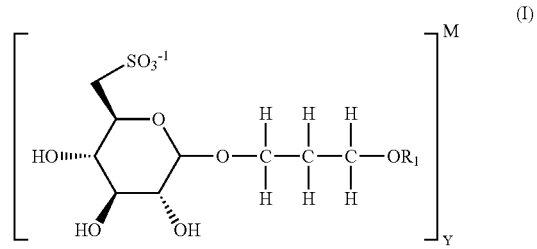

wherein $R_1$ is an acyl residue of a fatty acid, Y is a number of 1, 2 or 3, and M represents a cation having a positive charge equal to Y and pharmaceutically acceptable salts thereof are effective for treating tumors.

9 Claims, 7 Drawing Sheets

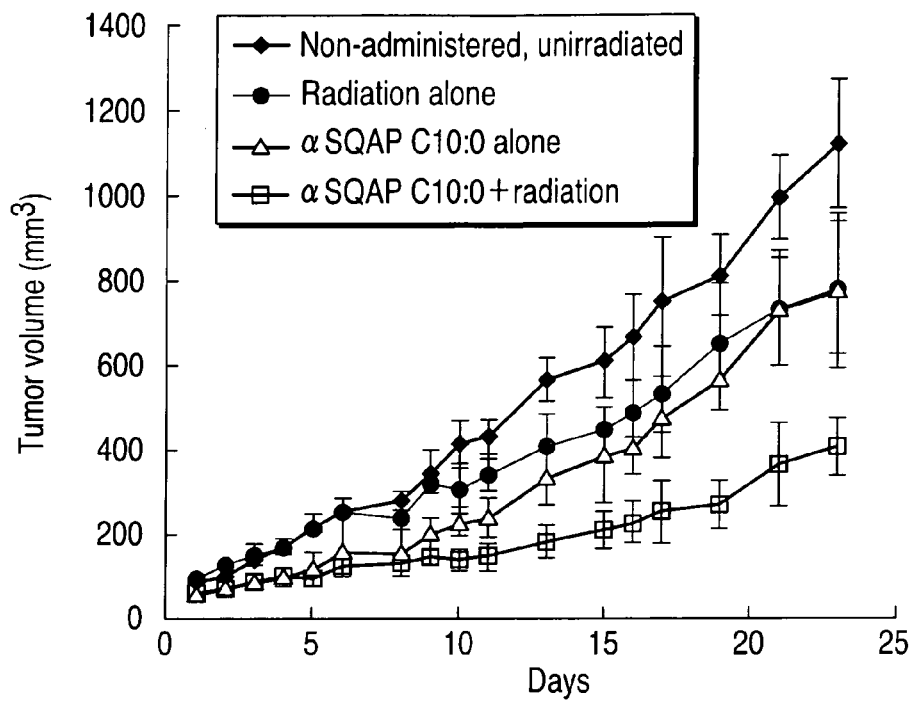
F I G. 7
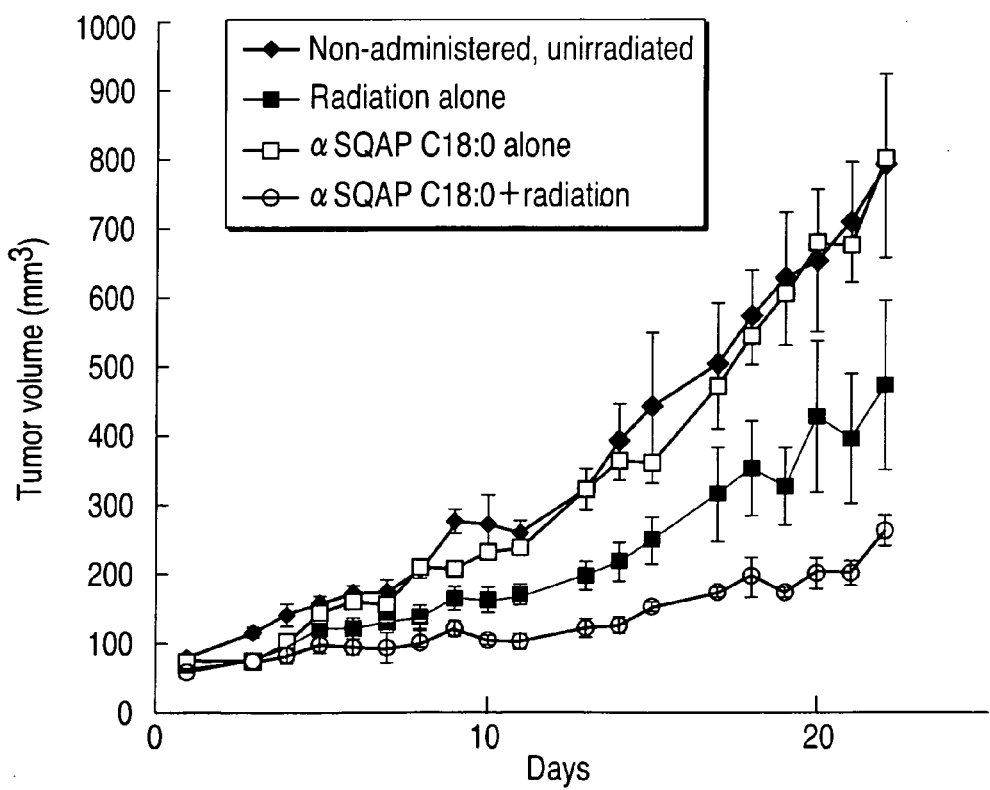
F I G. 8

SULFONATED SUGAR COMPOUNDS, PHARMACEUTICAL COMPOSITIONS WHICH CONTAIN THE SAME, AND METHODS OF TREATING TUMORS WITH THE SAME

CROSS REFERENCE TO RELATED APPLICATIONS

The present application is a continuation of International Application No. PCT/JP2008/063056, filed on Jul. 18, 2008, and claims priority to Japanese Patent Application No. 2007-190120, filed on Jul. 20, 2007, both of which are incorporated herein by reference in their entireties.

BACKGROUND OF THE INVENTION

1. Field of the Invention

The present invention relates to novel sulfonated sugar compounds and pharmaceutical compositions containing the same. The present invention also relates to novel methods of making such a compound and novel intermediates useful for making such a compound. The present invention further relates to novel methods for treating a tumor by administering such a compound.

2. Discussion of the Background

At present, in Japan, malignant tumors, cardiac disease, and cerebrovascular disease are responsible for about 60 percent of deaths. Among them, malignant tumor is the leading cause of death and is increasing. For treating malignant tumors, the three major therapies are surgical therapy, chemotherapy, and radiation therapy. In recent years, the quality of life (QOL) of a patient has been emphasized, and much attention is being paid to radiation therapy.

In common radiation therapy, halogenated pyrimidine and hypoxic cell sensitizers are known as chemical or pharmaceutical substances administered simultaneously with radiation thereby enhancing its therapeutic effect, more specifically, as clinically applicable radiosensitizers (for example, see Radiobiology for the Radiologist (Fourth Edition), Eric J. Hall et al, J. B. Lippincott Company ("Houshasennkainotameno Hoshasenseibutsugaku", translated by Muneyasu Urano, Shinoharashinsha. Inc.). Examples of known halogenated pyrimidines include 5-iododeoxyuridine. Examples of known hypoxic cell sensitizers include misonidazole. However, these known radiosensitizers are scarcely in actual use, because they produce side effects such as gastrointestinal disorders and peripheral neurotoxicity, and involve other outstanding problems.

On the other hand, novel radiosensitizers composed of sulfopyranosylacylglycerol or salts thereof are disclosed in Jpn. Pat. Appln. No. 2004-374445. However, in sulfopyranosylacylglycerols, the 2-position carbon atom in the glycerol moiety is an asymmetric carbon, so that the stereostructure cannot be controlled by a relatively inexpensive and simple synthesis process as described in Jpn. Pat. Appln. No. 2004-374445, in which the terminal double bond of an allyl group is dihydroxylated to form a glycerol skeleton. Therefore, R/S diastereomers are generated at a ratio of about 1:1. In order to solve the problem, respective diastereomers can be independently synthesized, but such process requires bonding of a glycerol derivative having a definite stereostructure to a sugar derivative during synthesis, which results in the complication of the synthesis process and an enormous increase of the cost.

In addition, a sulfopyranosylacylglycerol derivative generates an R/S diastereoisomer (diastereomers) at the 2-position of the glycerol moiety, as well as several percent of a structural isomer (2-acyl isomer) wherein the acyl group at the 1-position of glycerol has been transferred to the 2-position between and/or within the molecules. These 2-acyl isomers are generated during synthesis and storage in a solution. Therefore, even if the respective diastereomers are independently prepared, it is very difficult to provide a high purity sulfopyranosylacylglycerol derivative.

Although a sulfopyranosylacylglycerol derivative exhibits a noticeable radiosensitization effect, its development as a drug will entail very difficult situations due to problems with synthesis and physical properties.

SUMMARY OF THE INVENTION

Accordingly, it is one object of the present invention to provide a novel compounds which are useful for treating tumors.

It is another object of the present invention to provide novel pharmaceutical compositions which contain such a compound.

It is another object of the present invention to provide novel compounds which are useful as radiosensitizers.

It is another object of the present invention to provide novel pharmaceutical compositions which contain such a compound.

It is another object of the present invention to provide practicable novel sulfonated sugar compounds and drugs or pharmaceutical compositions containing the same, and specifically to provide a practicable novel sulfonated sugar compounds obtainable at high purity by a simple synthesis method, and drug or pharmaceutical compositions containing the same.

It is another object of the present invention to provide novel methods for preparing such compounds.

It is another object of the present invention to provide novel intermediates which are useful for preparing such compounds.

It is another object of the present invention to provide novel methods for treating a tumor.

It is another object of the present invention to provide novel methods of treating a tumor with radiation therapy.

As a result of dedicated research by the inventors, means for solving the above problems was found. Thus, the present invention provides:

(1) A sulfoquinovosylacyl propanediol compound represented by (I):

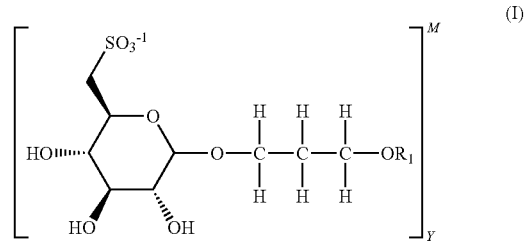

wherein $R_1$ is an acyl residue of a fatty acid, Y is a number of 1, 2 or 3, and M represents a cation having a positive charge equal to Y, or pharmaceutically acceptable salt thereof.

(2) An anion represented by formula (I'):

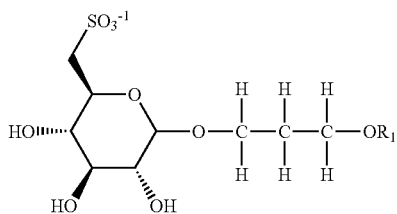

wherein $R_1$ is an acyl residue of a fatty acid.

(3) A pharmaceutical composition, comprising at least one sulfoquinovosylacyl propanediol compound or pharmaceutically acceptable salt thereof according to (1) and a pharmaceutically acceptable carrier.

(4) A pharmaceutical composition according to (3), which is a radiosensitizer.

(5) A pharmaceutical composition according to (3), which is an antineoplastic agent.

(6) A process for making a compound or pharmaceutically acceptable salt thereof according to (1), which comprises:
deprotecting a compound of formula (IX):

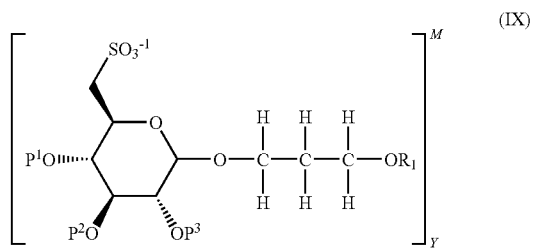

wherein $P^1$, $P^2$, and $P^3$ are each independently a protecting group, $R_1$ is an acyl residue of a fatty acid, Y is a number of 1, 2 or 3, and M represents a cation having a positive charge equal to Y, to obtain said compound or pharmaceutically acceptable salt thereof according to (1).

(7) A process according to (6), wherein said compound of formula (IX) is prepared by a process comprising:
oxidizing a compound of formula (VIII):

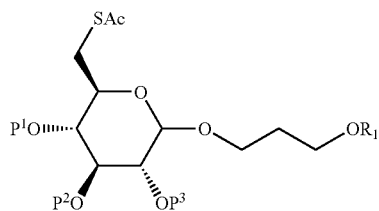

wherein $P^1$, $P^2$, and $P^3$ are each independently a protecting group, SAc is an acetylthio group, and $R_1$ is an acyl residue of a fatty acid, to obtain said compound of formula (IX).

(8) A process according to (7), wherein said compound of formula (VIII) is prepared by a process comprising:
reacting a compound of formula (VII):

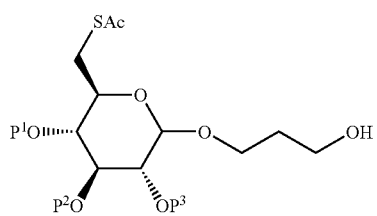

wherein $P^1$, $P^2$, and $P^3$ are each independently a protecting group, and SAc is an acetylthio group, with a compound of formula $R_1C(=O)L$, wherein $R_1$ is an acyl residue of a fatty acid and L is a leaving group, to obtain said compound of formula (VIII).

(9) A process according to (6), wherein said compound of formula (IX) is prepared by a process comprising:
reacting a compound of formula (X'):

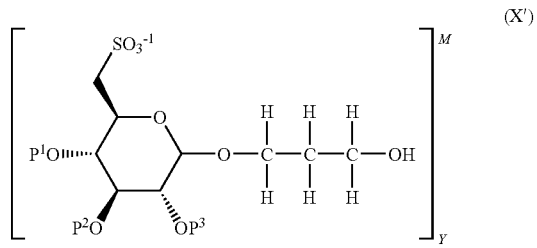

wherein $P^1$, $P^2$, and $P^3$ are each independently a protecting group, Y is a number of 1, 2 or 3, and M represents a cation having a positive charge equal to Y, with a compound of formula $R_1C(=O)L$, wherein $R_1$ is an acyl residue of a fatty acid and L is a leaving group, to obtain said compound of formula (IX).

(10) A process according to (9), wherein said compound of formula (X') is prepared by a process comprising:
converting a compound of formula (IX"):

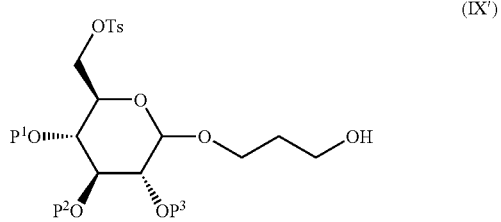

wherein $P^1$, $P^2$, and $P^3$ are each independently a protecting group, and Ts is a tosyl group, to said compound of formula (X').

(11) A compound represented by formula (VIII):

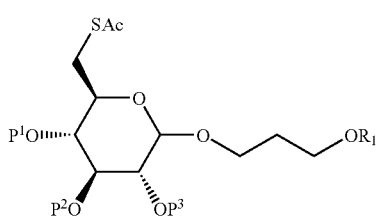

wherein $P^1$, $P^2$, and $P^3$ are each independently a protecting group, SAc is an acetylthio group, and $R_1$ is an acyl residue of a fatty acid.

(12) A compound represented by formula (IX):

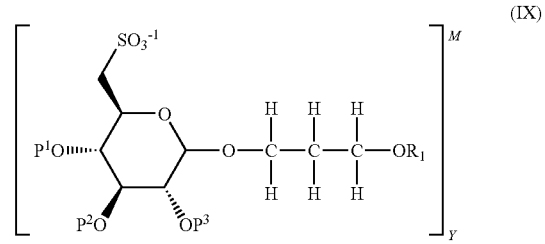

wherein $P^1$, $P^2$, and $P^3$ are each independently a protecting group, $R_1$ is an acyl residue of a fatty acid, Y is a number of 1, 2 or 3, and M represents a cation having a positive charge equal to Y.

(13) A compound represented by formula (X'):

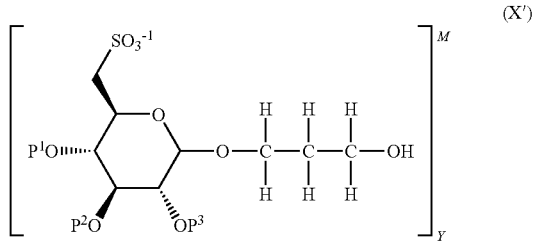

wherein $P^1$, $P^2$, and $P^3$ are each independently a protecting group, Y is a number of 1, 2 or 3, and M represents a cation having a positive charge equal to Y.

(14) A compound represented by formula (IX'):

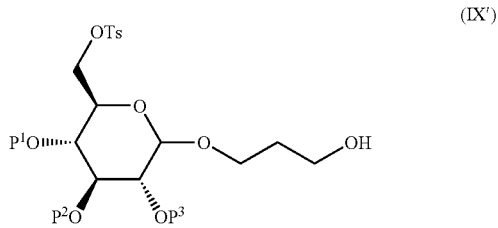

wherein $P^1$, $P^2$, and $P^3$ are each independently a protecting group, and Ts is a tosyl group.

(15) A process for making a compound or pharmaceutically acceptable salt thereof according to (1), which comprises:

reacting a compound of formula (IX"):

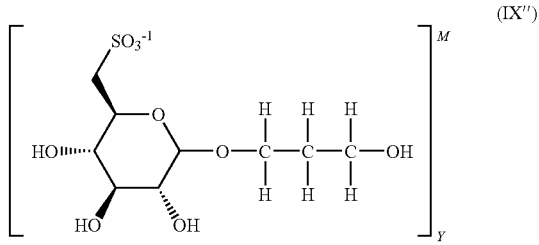

wherein Y is a number of 1, 2 or 3, and M represents a cation having a positive charge equal to Y, with a compound of formula $R_1C(=O)L$, wherein $R_1$ is an acyl residue of a fatty acid and L is a leaving group, to obtain said compound or pharmaceutically acceptable salt thereof according to (1).

(16) A process according to (15), wherein said compound of formula (IX") is prepared by a process comprising:

deprotecting a compound of formula (VIII"):

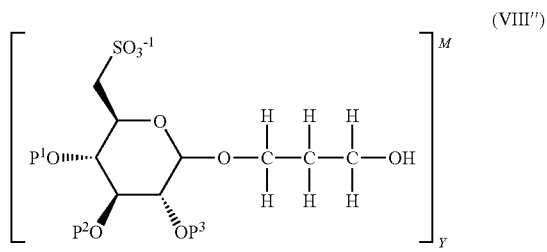

wherein $P^1$, $P^2$, and $P^3$ are each independently a protecting group, Y is a number of 1, 2 or 3, and M represents a cation having a positive charge equal to Y, to obtain said compound of formula (IX").

(17) A process according to (16), wherein said compound of formula (VIII") is prepared by a process comprising:

oxidizing a compound of formula (VII):

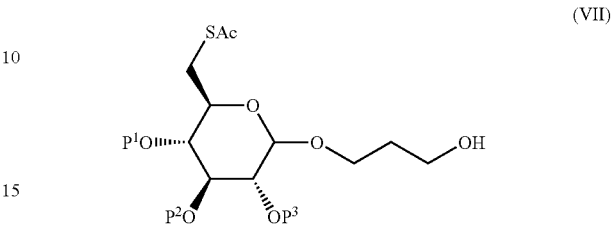

wherein $P^1$, $P^2$, and $P^3$ are each independently a protecting group and SAc is an acetylthio group, to obtain said compound of formula (VIII").

(18) A compound represented by formula (VIII"):

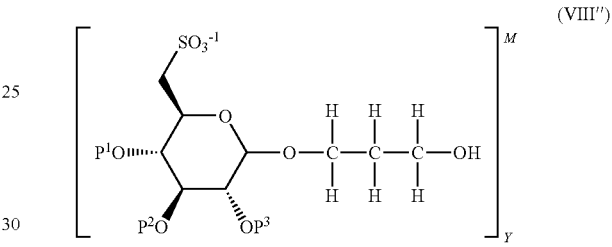

wherein $P^1$, $P^2$, and $P^3$ are each independently a protecting group, Y is a number of 1, 2 or 3, and M represents a cation having a positive charge equal to Y.

(19) A compound represented by formula (IX"):

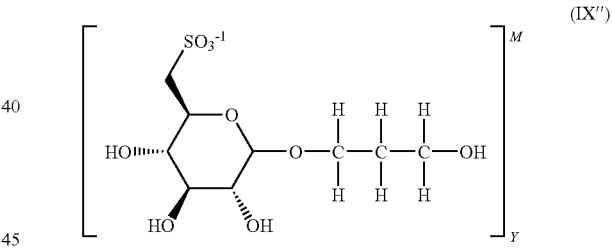

wherein Y is a number of 1, 2 or 3, and M represents a cation having a positive charge equal to Y.

(20) A method of treating a tumor, comprising administering an effective amount of a compound according to (1) or a pharmaceutically acceptable salt thereof to a subject in need thereof.

The present invention provides a practicable novel sulfonated sugar compound and a drug including the same. Specifically, the present invention provides a novel sulfonated sugar compound obtainable at high purity by a simple synthesis method, and a drug including the same.

A benefit of the present invention will be described in the following description, and will be partially defined by the description or an embodiment of the present invention. A benefit of the present invention will be understood and achieved through drawings and below-described combinations.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 7 is a graph showing the effect of a test substance on the increase of tumor volume.

FIG. 8 is a graph showing the effect of a test substance on the increase of tumor volume.

DETAILED DESCRIPTION OF THE PREFERRED EMBODIMENTS

Figure 1:
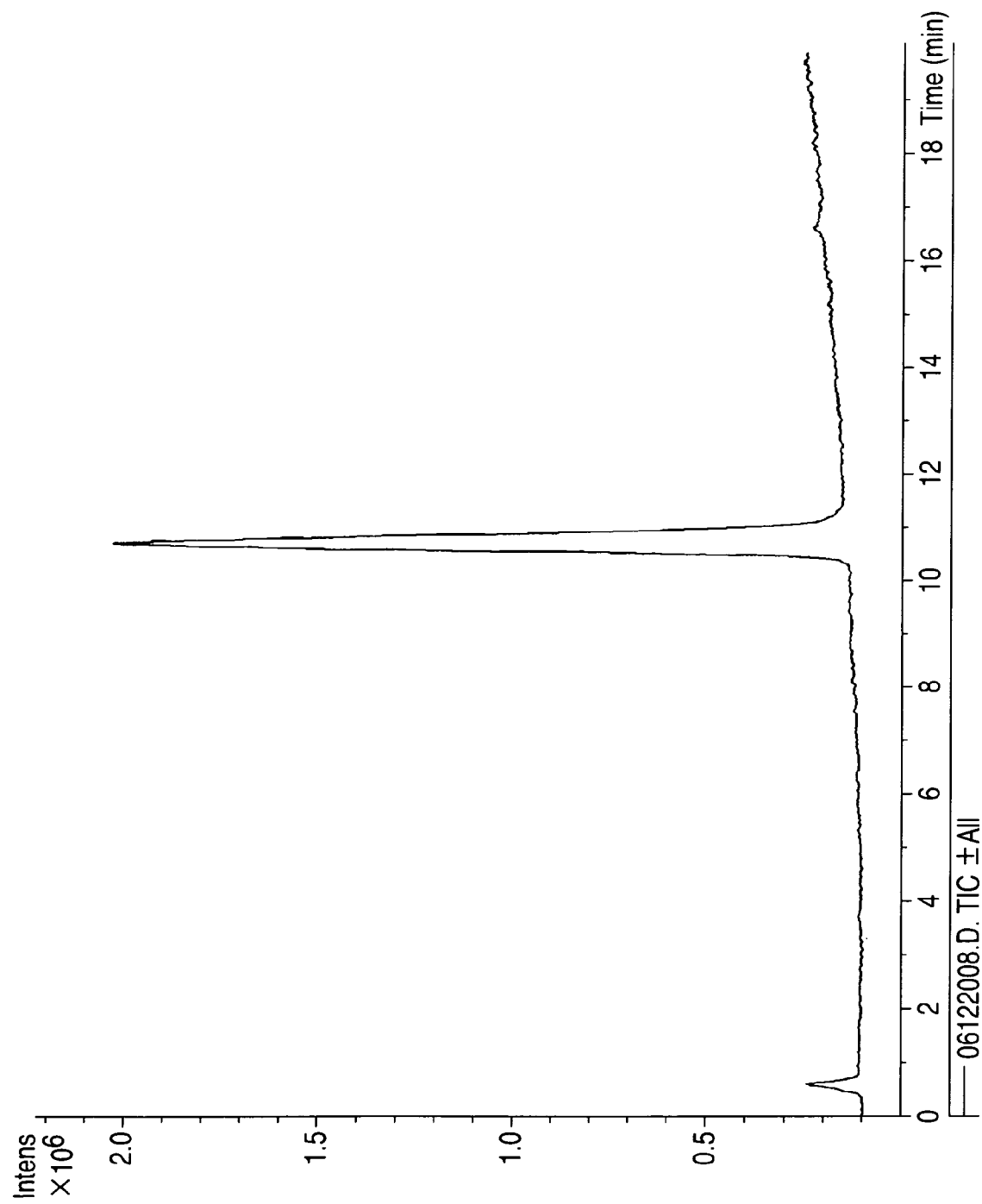
FIG. 1 is a chromatogram showing the result of analysis of αSQAP C18:0.

According to one aspect of the present invention, the sulfoquinovosylacyl propanediol compound expressed by formula (I) and pharmaceutically acceptable salts thereof are provided:

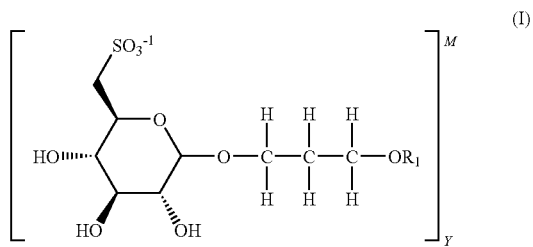

wherein $R_1$ is an acyl residue of a fatty acid, Y is a number of 1, 2 or 3, and M represents a cation having a positive charge equal to Y.

In the present invention, when the "$R_1$" is an acyl residue of a fatty acid, the number of carbons contained therein is 26 or less and 1 or more, and preferably 22 or less. The fatty acid for providing the acyl residue of a fatty acid according to the present invention may be a linear or branched, saturated or unsaturated fatty acid, and each occurrence of unsaturation may be in either the cis or trans or in the Z or E configuration.

Specific examples of $R_1$ include, but are limited to, methanoyl (formyl), ethanoyl (actyl), n-propoanoyl (n-propionyl), i-propoanoyl (i-propionyl), n-butanoyl, iso-butanoyl, sec-butanoyl, tert-butanoyl, n-pentanoly, iso-pentanoly, sec-pentanoyl, tert-pentanoyl, neo-pentanoyl, n-hexanoyl, iso-hexanolyl, sec-hexanoyl, tert-hexanoyl, neo-hexanoyl, n-heptanoyl, iso-heptanoyl, sec-heptanoyl, tert-heptanoyl, neo-heptanoyl, n-octanoyl, iso-octanoyl, sec-octanoyl, tert-octanoyl, neo-octanoyl, n-nonanoyl, iso-nonanoyl, sec-nonanoyl, tert-nonanoyl, neo-nonanoyl, n-decanoyl, iso-decanoyl, sec-decanoyl, tert-decanoyl, neo-decanoyl, n-undecanoyl, iso-undecanoyl, sec-undecanoyl, tert-undecanoyl, neo-undecanoyl, n-dodecanoyl, iso-dodecanoyl, sec-dodecanoyl, tert-dodecanoyl, neo-dodecanoyl, n-tridecanoyl, iso-tridecanoyl, sec-tridecanoyl, tert-tridecanoyl, neo-tridecanoyl, n-tertradecanoyl (myristoyl), iso-tertradecanoyl, sec-tertradecanoyl, tert-tertradecanoyl, neo-tertradecanoyl, n-pentadecanoyl, iso-pentadecanoyl, sec-pentadecanoyl, tert-pentadecanoyl, neo-pentadecanoyl, n-hexadecanoyl (palmitoyl), iso-hexadecanoyl, sec-hexadecanoyl, tert-hexadecanoyl, neo-hexadecanoyl, n-heptadecanoyl, iso-heptadecanoyl, sec-heptadecanoyl, tert-heptadecanoyl, neo-heptadecanoyl, n-octadecanoyl (stearoyl), iso-octadecanoyl, sec-octadecanoyl, tert-octadecanoyl, neo-octadecanoyl, n-nonadecanoyl, iso-nonadecanoyl, sec-nonadecanoyl, tert-nonadecanoyl, neo-nonadecanoyl, n-eicosanoyl, iso-eicosanoyl, sec-eicosanoyl, tert-eicosanoyl, neo-eicosanoyl, n-heneicosanoyl, iso-heneicosanoyl, sec-heneicosanoyl, tert-heneicosanoyl, neo-heneicosanoyl, n-docosanoyl, iso-docosanoyl, sec-docosanoyl, tert-docosanoyl, neo-docosanoyl, n-tricosanoyl, iso-tricosanoyl, sec-tricosanoyl, tert-tricosanoyl, neo-tricosanoyl, n-pentacosanoyl, iso-pentacosanoyl, sec-pentacosanoyl, tert-pentacosanoyl, neo-pentacosanoyl, n-hexacosanoyl, iso-hexacosanoyl, sec-hexacosanoyl, tert-hexacosanoyl, neo-hexacosanoyl, myristoleoyl, plamitoleoyl, oleoyl, linoleoyl, α-linoleoyl, arachidonoyl, euricoyl, and docosahexaenoyl. Of course, it is possible for the compound of formula (I) to exist as a mixture of compounds which contain two or more different acyl groups for $R_1$.

The quinovose ring contained in the sulfoquinovosylacyl propanediol compound according to the present invention may exist in a boat form, a chair form, or a mixed conformation, but typically exists in a chair form because it is usually stable. The steric configuration of the propanediol site in the quinovose ring may be an α anomer, a β anomer, or a mixture thereof.

The sulfoquinovosylacyl propanediol compound according to the present invention may be hereinafter referred to as "SQAP" or "SQAP compound". In the term "αSQAP Cm:n", "α" represents an α anomer, and "Cm:n" describes the group $R_1$, where the number of carbon atoms contained in the $R_1$ group of SQAP is "m", and the number of double bond(s) in the $R_1$ group is "n", wherein "m" is an integer of 1 or more, and "n" is an integer of 0 or more. Accordingly, for example, "αSQAP C18:0" represents an α anomer of sulfoquinovosylacyl propanediol wherein the number of carbon atoms contained in the acyl residue of the fatty acid is 18, and the number of double bonds is 0.

Y is an integer which is 1, 2, or 3 and will depend on the positive charge of the cation, M.

M may be any cation which has a charge of +1, +2 or +3. Preferred are pharmaceutically acceptable cations. Specific examples of suitable cations include, but are not limited to, proton ($H^+$), lithium ($Li^+$), sodium ($Na^+$), potassium ($K^+$), calcium ($Ca^{+2}$), magnesium ($Mg^{+2}$), manganese ($Mn^{+2}$ and $Mn^{+3}$), iron ($Fe^{+2}$ and $Fe^{+3}$), zinc ($Zn^{+2}$), copper ($Cu^{+1}$, $Cu^{+2}$, and $Cu^{+3}$), strontium ($Sr^{+2}$), lead ($Pb^{+2}$), silver ($Ag^+$), barium ($Ba^{+2}$), aluminum ($Al^{+3}$), chromium ($Cr^{+2}$ and $Cr^{+3}$), cobalt ($Co^{+2}$ and $Co^{+3}$), nickel ($Ni^{+2}$ and $Ni^{+3}$), ammonium, mono-, di-, tri-, and tetra-($C_{1-4}$)-alkylammonium, and mono-, di-, tri-, and tetra-($C_{1-4}$)-hydroxyalkylammonium.

The compound of formula (I) may also exist as a pharmaceutically acceptable salt, such as an acid addition salt or a salt in which one of the hydroxyl hydrogens is replaced by a cation.

In another embodiment, the present invention provides anions of the formula (I'):

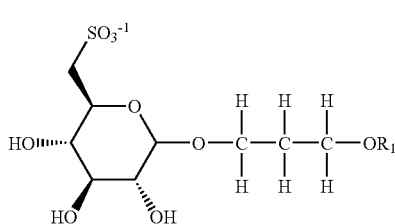
(I')

wherein $R_1$ is the same acyl residue of a fatty acid as described in connection with the compound of formula (I).

In another embodiment, the present invention provides intermediates which are useful for preparing the compounds of formula (I). One such intermediate is represented by formula (VIII):

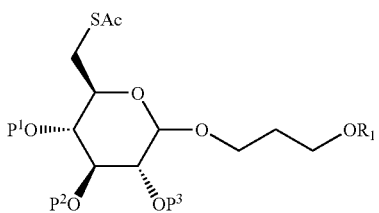
(VIII)

wherein $P^1$, $P^2$, and $P^3$ are each independently a protecting group, SAc is an acetylthio group, and $R_1$ is the same acyl residue of a fatty acid as described in connection with formula (I).

Another such intermediate is the compound represented by formula (IX):

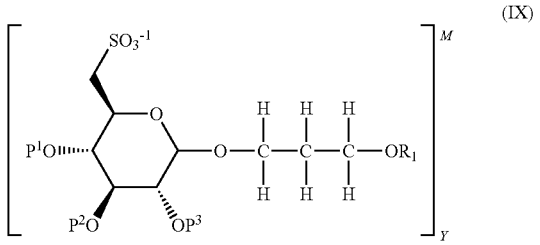
(IX)

wherein $P^1$, $P^2$, and $P^3$ are each independently a protecting group, $R_1$ is the same acyl residue of a fatty acid as described in connection with formula (I), Y is a number of 1, 2 or 3, and M represents the same cation as described in connection with formula (I).

Another intermediate is the compound represented by formula (X'):

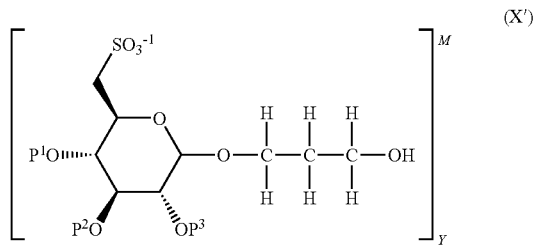
(X')

wherein $P^1$, $P^2$, and $P^3$ are each independently a protecting group, Y is a number of 1, 2 or 3, and M represents a cation having a positive charge equal to Y.

Another such intermediate is the compound represented by formula (IX'):

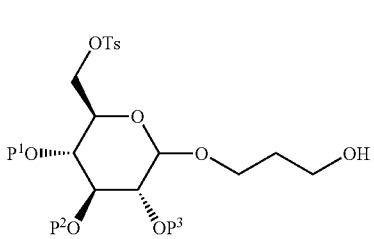
(IX')

wherein $P^1$, $P^2$, and $P^3$ are each independently a protecting group, and Ts is a tosyl group.

Another such intermediate is the compound represented by formula (VIII"):

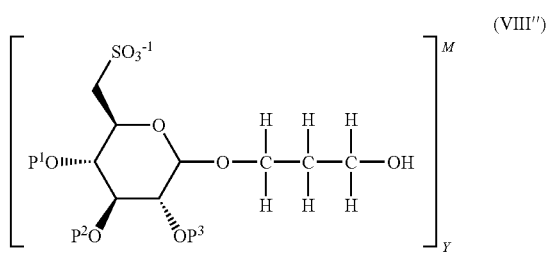
(VIII")

wherein $P^1$, $P^2$, and $P^3$ are each independently a protecting group, Y is a number of 1, 2 or 3, and M represents the same cation as described in connection with formula (I).

Another such intermediate is the compound represented by formula (IX"):

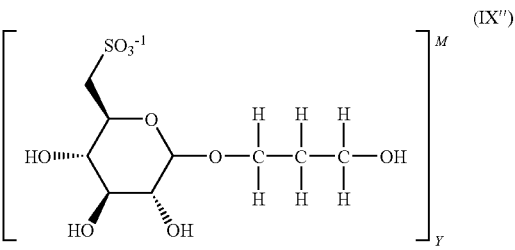
(IX")

wherein Y is a number of 1, 2 or 3, and M represents the same cation as described in connection with formula (I).

In the compounds of formulae (VIII), (IX), (X'), (IX'), and (VIII"), $P^1$, $P^2$, and $P^3$ are each independently a protecting group. Any protecting group suitable for protecting a hydroxyl group may be used. Such groups are described in Philip Kocienski, Protecting Groups, 3rd Edition, Georg Thieme Verlag, 2003; and Theodora W. Greene and Peter G. M. Wuts, Protective Groups in Organic Synthesis, 3rd Edition, John Wiley & Sons Inc., 1999, both of which are incorporated herein by reference. Particularly preferred protecting groups include benzyl groups, p-methoxybenzyl groups, 3,4-dimethoxybenzyl groups, 2,6-dimethoxybenzyl groups, p-phenylbenzyl groups, and 2-phenyl-2-propyl groups.

In another embodiment, the present invention provides methods for preparing the compounds of formula (I). One such method involves:

A process for making a compound or pharmaceutically acceptable salt thereof according to (1), which comprises:

deprotecting a compound of formula (IX):

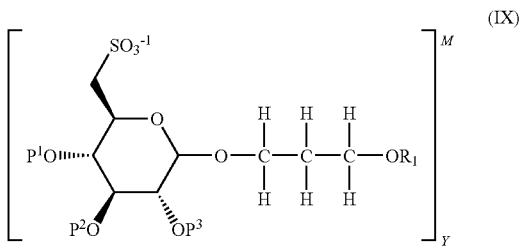

wherein $P^1$, $P^2$, and $P^3$ are each independently a protecting group, $R_1$ is the same acyl residue of a fatty acid as described in connection with the compound of formula (I), Y is a number of 1, 2 or 3, and M represents the same cation as described in connection with formula (I), to obtain said compound or pharmaceutically acceptable salt thereof according to (1).

The deprotection of the compound of formula (IX) may be achieved by any suitable means, depending on the exact identity of the protecting groups. See, Philip Kocienski, Protecting Groups, 3rd Edition, Georg Thieme Verlag, 2003; and Theodora W. Greene and Peter G. M. Wuts, Protective Groups in Organic Synthesis, 3rd Edition, John Wiley & Sons Inc., 1999, both of which are incorporated herein by reference. When the protecting groups are benzyl groups, good results are achieved by catalytic hydrogenation, using a catalyst such as platinum, rhodium, ruthenium, palladium activated carbon, Raney nickel, etc.

In one preferred embodiment, the compound of formula (IX) is prepared by a process comprising:

oxidizing a compound of formula (VIII):

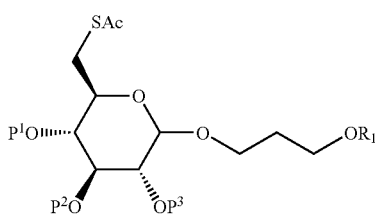

wherein $P^1$, $P^2$, and $P^3$ are defined above, SAc is an acetylthio group, and $R_1$ is the same acyl residue of a fatty acid as described in connection with the compound of formula (IX).

The oxidation of the compound of formula (VIII) may be carried out with any suitable oxidizing agent. Examples of suitable oxidizing agents include, but are not limited to, OXONE® (2 $KHSO_5 \cdot KHSO_4 \cdot K_2SO_4$), $H_2O_2 \cdot HCOOH$, $H_2O_2 \cdot CH_3COOH$, $H_2O_2 \cdot CF_3COOH$, $H_2O_2 \cdot H_2O$ and dimethyldioxirane. Particularly good results have been achieved by using potassium peroxymonosulfate, $KHSO_5$, such as Oxone®, which is commercially available from DuPont. The oxidation may be carried out in any suitable solvent and under time and temperature conditions suitable for obtaining the compound of formula (IX).

In another preferred embodiment, the compound of formula (VIII) is prepared by a process comprising:

reacting a compound of formula (VII):

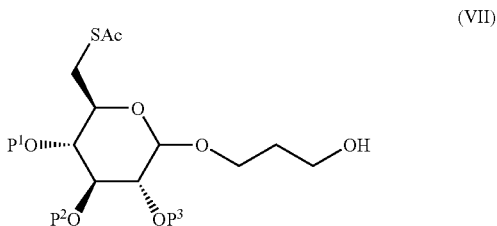

wherein $P^1$, $P^2$, $P^3$, and SAc are as defined above, with a compound of formula $R_1C(=O)L$, wherein $R_1$ is the same acyl residue of a fatty acid as described in connection with the compound of formula (I), and L is a leaving group.

In the compound of formula $R_1C(=O)L$, L may be any leaving group, which is suitable for reacting with the hydroxyl group in the compound of formula (VII) to form the compound of formula (VIII). Suitable examples include, but are not limited to, fluoride, chloride, bromide, and iodide. In addition, L may be a group of the formula $R_1C(=O)$—, such that the compound of formula $R_1C(=O)L$ is an acid anhydride. Further, L may be an alcohol moiety, such that the compound of formula $R_1C(=O)L$ is an active ester, such as an N-hydroxyphthalimide ester or a 2,4,6-trimethylbenzyl ester.

The reaction of the compound of formula (VII) with the compound of formula $R_1C(=O)L$, may be carried out in any suitable solvent, such as dichloromethane, chloroform, benzene, toluene, etc. This step may also be carried out in the presence of a base, such pyridine, etc. The molar ratio of the compound of formula (VII) to the compound of formula $R_1C(=O)L$ may be approximately 1:1 or the compound of formula $R_1C(=O)L$ may be used in a slight excess. The reaction time and temperature may be suitably adjusted to achieve the desired compound in good amount in a convenient time.

In another preferred embodiment, the compound of formula (IX) is prepared by a process comprising:

reacting a compound of formula (X'):

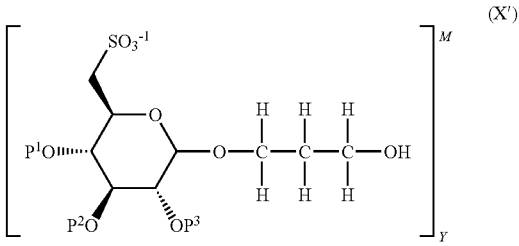

wherein $P^1$, $P^2$, and $P^3$ are each independently a protecting group, Y is a number of 1, 2 or 3, and M represents a cation having a positive charge equal to Y, with a compound of formula $R_1C(=O)L$, wherein $R_1$ is an acyl residue of a fatty acid and L is a leaving group.

The reaction of the compound of formula (X') with the compound of formula $R_1C(=O)L$, may be carried out in substantially the same way as the reaction of the compound of formula (VII) with the compound of formula $R_1C(=O)L$. Thus, this reaction may be carried out in any suitable solvent, and molar ratio of reactants, the reaction time and temperature may be suitably adjusted to achieve the desired compound in good amount in a convenient time. In this particularly good results have been achieved by reacting the compound of formula (X') with a fatty acid of formula R₁C(=O)OH in a solvent of N,N-dimethylformamide and in the presence of 1-ethyl-3-(3-dimethylaminopropyl)carbodiimide hydrochlorid and 4-dimethylaminopyridine.

In another preferred embodiment, the compound of formula (X') is prepared by a process comprising:
converting a compound of formula (IX'):

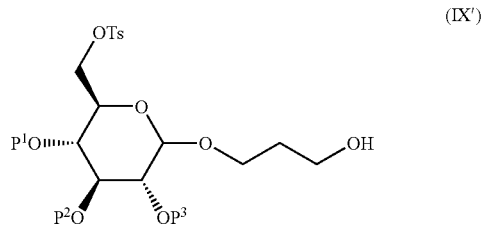
(IX')

wherein $P^1$, $P^2$, and $P^3$ are defined above and Ts is a tosyl group, to said compound of formula (X').

The conversion of the compound of formula (IX') to the compound of formula (X') may be carried out with any suitable reagent, such as sodium sulfite, and in any suitable solvent, such as ethanol, water, and mixtures thereof.

In another embodiment, the compounds and pharmaceutically acceptable salts of formula (I) may be prepared by a process involving:
reacting a compound of formula (IX"):

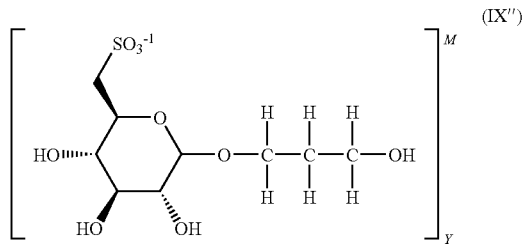
(IX")

wherein Y is a number of 1, 2 or 3, and M represents a cation having a positive charge equal to Y, with a compound of formula R₁C(=O)L, wherein R₁ is an acyl residue of a fatty acid and L is a leaving group.

In this case, the leaving groups may be the same as described above, and the reaction of the compound of formula (IX") with the compound of formula R₁C(=O)L may be carried out in substantially the same way as the reaction of the compound of formula (X') with the compound of formula R₁C(=O)L.

In another preferred embodiment, the compound of formula (IX") is prepared by a process comprising:
deprotecting a compound of formula (VIII"):

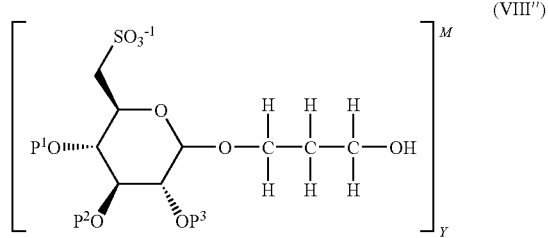
(VIII")

wherein $P^1$, $P^2$, and $P^3$ are each independently a protecting group, Y is a number of 1, 2 or 3, and M represents a cation having a positive charge equal to Y. In this case, the protecting groups may be the same as described above, and the deprotection of the compound of formula (VIII") may be carried in substantially the same way as the deprotection steps described above.

In another preferred embodiment, the compound of formula (VIII") is prepared by a process comprising:
oxidizing a compound of formula (VII):

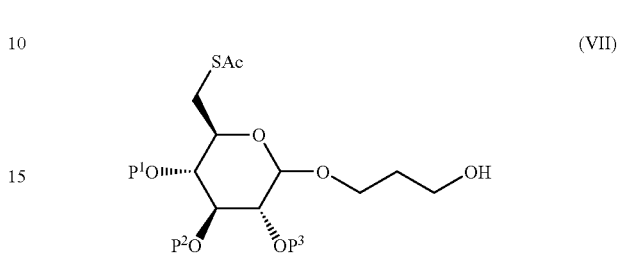
(VII)

wherein $P^1$, $P^2$, and $P^3$ are defined above and SAc is an acetylthio group.

In this case, the oxidation of the compound of formula (VII) may be carried out substantially as described above for compound (VIII).

The method for preparing the sulfoquinovosylacyl propanediol compound according to the present invention may be, but is not limited to, the following detailed methods described below. Since the sulfoquinovosylacyl propanediol compound according to the present invention will not generate new asymmetric carbon during the synthesis process, the compound can be prepared easily, simply, and at high purity. In addition, the compound can be stored in a structurally stable state, because there is no hydroxy group, which readily causes transfer, present near the R₁ group.

In the following scheme, "Ph" represents a phenyl group, "Bn" represents a benzyl group, "Ts" represents a tosyl group, "SAc" represents an acetylthio group, and "M" represents a hydrogen ion or a metal ion.

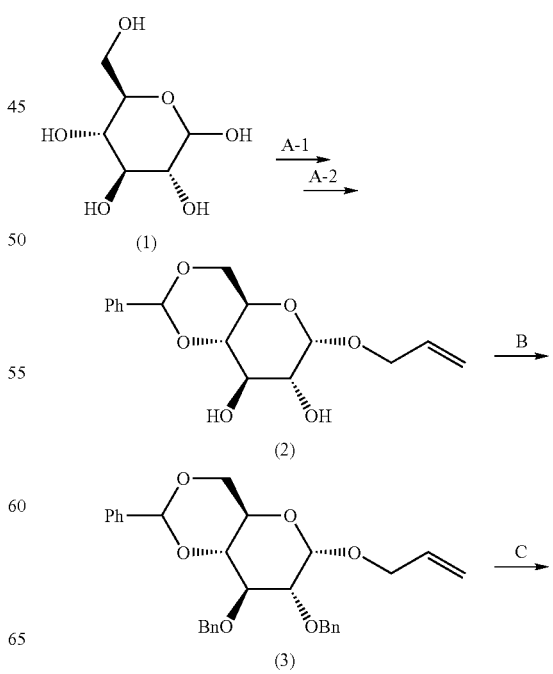

-continued

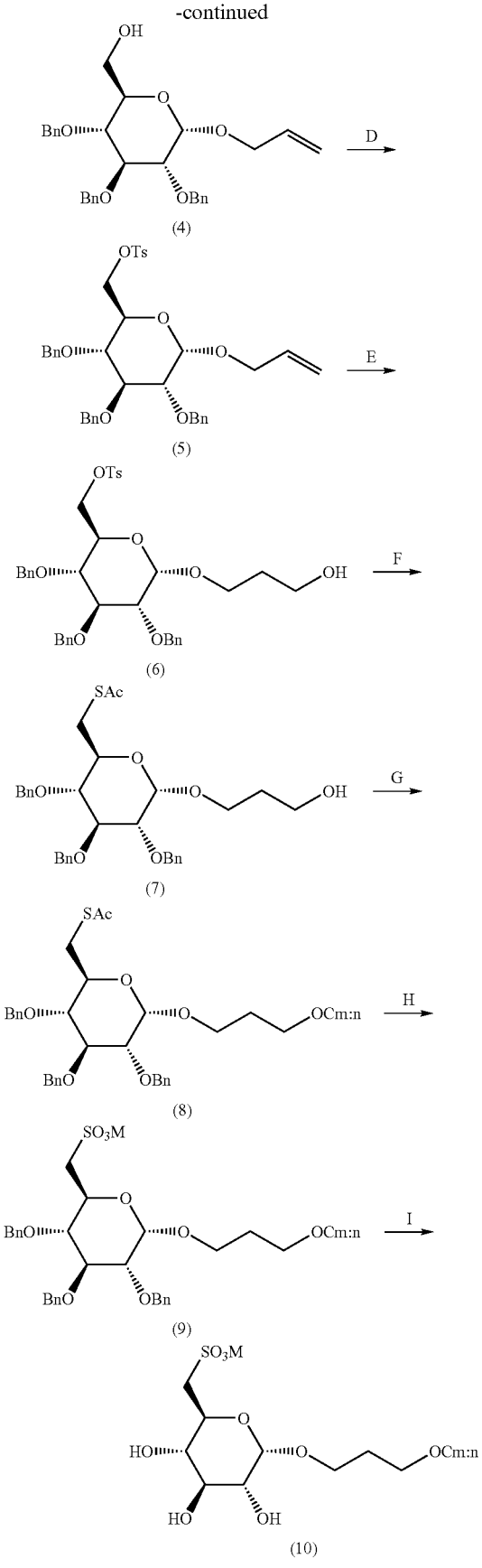

In the scheme shown above, the steps A through I involve:
A) A-1. allyl alcohol, trifluoromethanesulfonic acid, 80° C., 48 hours;
A-2. benzaldehyde dimethyl acetal, p-toluenesulfonic acid monohydrate, acetonitrile, 40° C., 4 hours;
B) benzyl bromide, sodium hydroxide, N,N-dimethylformamide, room temperature, 24 hours;
C) lithium hydride aluminum, aluminum chloride, dichloromethane, diethyl ether, heating under reflux, 4 hours;
D) p-toluenesulfonyl chloride, 4-dimethylaminopyridine, pyridine, room temperature;
E) 9-borabicyclononane, tetrahydrofuran, room temperature, 10 hours; water, sodium hydroxide, hydrogen peroxide water, room temperature, 12 hours;
F) potassium thioacetate, N,N-dimethylformamide, 90° C., 3 hours;
G) fatty acid derivative, pyridine, dichloromethane, room temperature, 2 hours;
H) Oxone®, acetic acid, potassium acetate, room temperature, 48 hours; and
I) palladium activated carbon, hydrogen gas, ethanol, dichloromethane, room temperature, 48 hours.

Alternatively, after the compound (7) is prepared via the route including the steps A to F, the intended compound (10) may be obtained via the following steps:

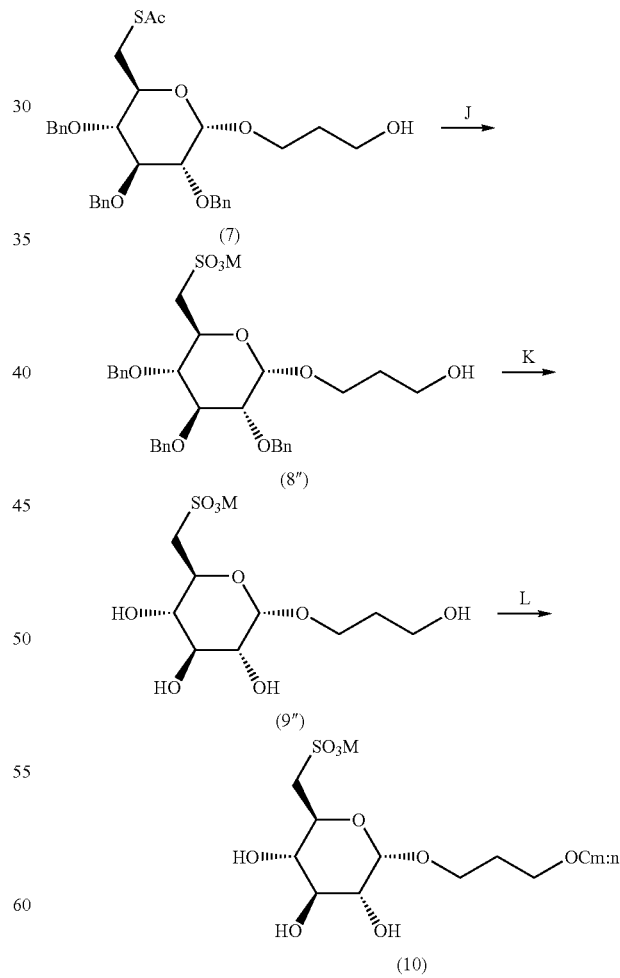

J) Oxone®, acetic acid, potassium acetate, room temperature, 48 hours;
K) palladium activated carbon, hydrogen gas, methanol, dichloromethane, room temperature, 16 hours; and L) fatty acid, 1-ethyl-3-(3-dimethylaminopropyl)carbodiimide hydrochloride, 4-dimethylaminopyridine, N,N-dimethylformamide, from 0° C. to room temperature, 18 hours.

The method for preparing the sulfoquinovosylacyl propanediol compound according to the present invention is not limited to the above-given specific example, and the following additional detailed method may be used instead.

In the next scheme, "Ac" represents an acetyl group, "MP" represents a p-methoxyphenyl group, "PMB" represents a p-methoxybenzyl group, "Ts" represents a tosyl group, and "M" represents a hydrogen ion or a metal ion.

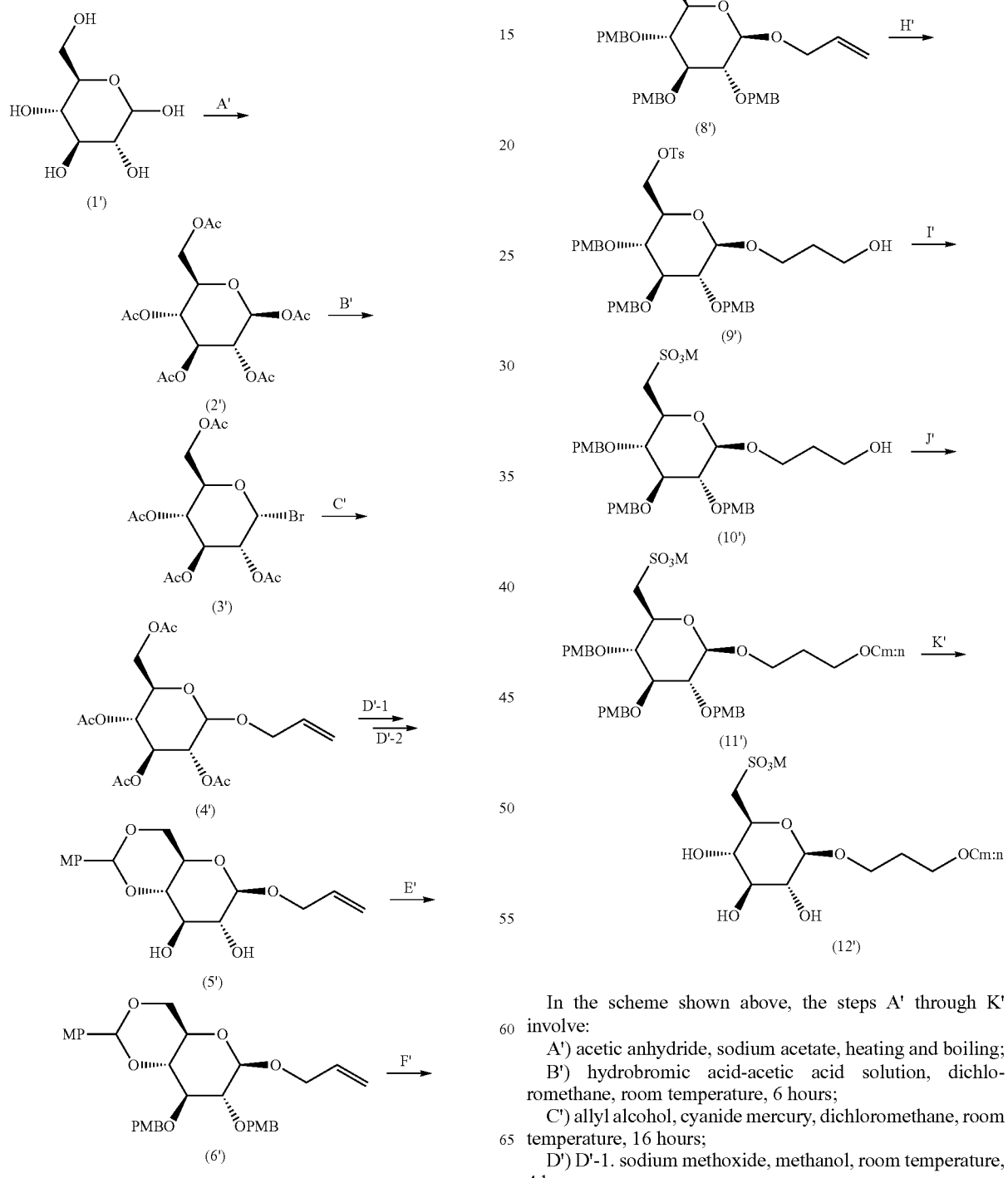

In the scheme shown above, the steps A' through K' involve:

A') acetic anhydride, sodium acetate, heating and boiling;
B') hydrobromic acid-acetic acid solution, dichloromethane, room temperature, 6 hours;
C') allyl alcohol, cyanide mercury, dichloromethane, room temperature, 16 hours;
D') D'-1. sodium methoxide, methanol, room temperature, 4 hours;

D'-2. p-anisaldehyde dimethyl acetal, p-toluenesulfonic acid monohydrate, acetonitrile, 40° C., 16 hours;

E') p-methoxybenzyl chloride, sodium hydroxide, N,N-dimethylformamide, room temperature, 16 hours;

F') lithium hydride aluminum, aluminum chloride, dichloromethane, diethyl ether, 0° C., 1 hour;

G') p-toluenesulfonyl chloride, 4-dimethylaminopyridine, pyridine, room temperature, 16 hours;

H') 9-borabicyclo nonane, tetrahydrofuran, room temperature, 16 hours; water, sodium hydroxide, hydrogen peroxide water, room temperature, 4 hours;

I') sodium sulfite, ethanol, water, heating under reflux, 72 hours;

J') fatty acid derivative, 4-dimethylaminopyridine, pyridine, dichloromethane, heating under reflux, 16 hours; and K') 2,3-dichloro-5,6-dicyano-1,4-benzoquinone, dichloromethane, methanol, water, room temperature, 4 hours.

Alternatively, any procedures known to those skilled in the art may be combined thereby preparing the sulfoquinovosylacyl propanediol compound and pharmaceutically acceptable salts thereof according to an aspect of the present invention. These preparation methods are also included in the scope of the present invention.

Examples of the sulfoquinovosylacyl propanediol compound expressed by the general formula (I) and pharmaceutically acceptable salts thereof according to the present invention include, but are not limited to, salts of monovalent cations such as sodium and potassium, and salts of divalent cations such as calcium and magnesium.

The salts according to the present invention may be prepared by the above-described synthesis method, or a modification of the synthesis method. Alternatively, the product synthesized by the above-described method may be subjected to a known ion exchange treatment to obtain the desired salt. These methods for synthesizing the salts according to the present invention are also included within the scope of the present invention.

The sulfoquinovosylacyl propanediol compound and pharmaceutically acceptable salts thereof according to the present invention have notable pharmacological effects such as radiation sensitizing effects and antineoplastic effects.

Therefore, according to another aspect of the present invention, the sulfoquinovosylacyl propanediol compound and pharmaceutically acceptable salts thereof may be provided as drugs utilizing their pharmacological effects.

Thus, according to another aspect of the present invention, the sulfoquinovosylacyl propanediol compound and pharmaceutically acceptable salts thereof have sensitizing effects as a first pharmacological effect. Accordingly, the sulfoquinovosylacyl propanediol compound and pharmaceutically acceptable salts thereof may be provided as radiosensitizers.

The radiosensitizer according to the present invention may be used for treating malignant neoplasm. Examples of malignant neoplasm include, but are not limited to, neurogenic tumors such as cerebral tumor; squamous cell carcinoma and adenocarcinoma, such as head and neck cancer, skin cancer, esophagus cancer, thyroid cancer, stomach cancer, lung cancer, gallbladder cancer, biliary tract cancer, pancreas cancer, liver cancer, prostate cancer, uterus cancer, ovarian cancer, breast cancer, kidney cancer, bladder cancer, and colon cancer; and melanoma, osteoma, soft tissue tumors, and lymphoma, leukemia, and myeloma. The term "treatment" used herein refers to the reduction, destruction, and/or inhibition of enhancement (growth) of the above-described malignant neoplasm.

The radiosensitizer according to the present invention may contain, as an active ingredient, an effective dose of at least one compound selected from the group consisting of the sulfoquinovosylacyl propanediol compounds expressed by the general formula (I) and pharmaceutically acceptable salts thereof. The radiosensitizer may contain more than one kind of compounds having different substituents $R_1$ in the general formula (I). In addition, the radiosensitizer may be combined with other radiosensitizer(s), an antitumor agent(s), or other substance having pharmacological activity and/or pharmaceutical activity without affecting its activity.

Hereinafter, the compounds consisting of the sulfoquinovosylacyl propanediol compound expressed by the general formula (I) and pharmaceutically acceptable salts thereof according to the present invention may be referred to as "radiosensitizing substance of the present invention".

The radiosensitizing substance of the present invention may be given by, for example, oral administration or parenteral administration. According to these administration routes, the radiosensitizing substance of the present invention may be combined with an appropriate pharmaceutically acceptable drug additive such as an excipient or diluent thereby making a pharmaceutical preparation. The radiosensitizer according to the present invention shall contain an effective dose of the radiosensitizing substance of the present invention, and may be provided as a pharmaceutical preparation as described above.

Examples of dosage forms suitable for oral administration include solid, semi-solid, liquid, and gas forms, and specific examples of thereof include, but are not limited to, tablets, capsules, powders, granules, solutions, suspending agents, syrups, elixirs, and aerosols.

When the radiosensitizing substance of the present invention is parenterally administered, it may be given by, for example, injection, transdermal administration, rectal administration, or ocular administration.

Administration by injection may be conducted through, for example, hypodermic, intradermal, intravenous, or intramuscular injection.

The conditions for administering the radiosensitizing substance of the present invention (for example, dose, frequency of administration, and interval of administration) may be appropriately established and adjusted according to the dosage form, administration route, disease to be treated, for example, state of malignant neoplasm (for example, type, location, and stage), conditions such as the drug to be combined (for example, presence or absence of combined drug, type, dose, frequency, and timing of administration of combined drug, and sequence of administration of the combined drug and the radiosensitizing substance of the present invention), the manner of combination with radiation (for example, the timing of combination and the order of the administration of the radiosensitizing substance of the present invention), and the conditions of the subject to be treated (for example, body weight, sex, and age).

For example, the dose of the radiosensitizing substance may be, but is not limited to, from 0.001 to 100 mg/kg body weight per day via oral administration, 0.001 to 50 mg/kg body weight per day via injection, from 0.001 to 100 mg/kg body weight per day via transdermal administration, 0.001 to 50 mg/kg body weight per day via rectal administration, or instillation of an about 0.001 to 3 wt. % solution several times a day via ocular administration.

In the radiotherapy treatment, the type, dose, and frequency of radiation may follow the conditions for conventional radiotherapy treatment. Specifically, conventional radiotherapy treatment for human is conducted through, for example, exposure to medical radiation such as an X ray, γ ray, electron ray, β ray, or other particle beams such as π-meson, neutron, or heavy particle beams with an irradiation dose of about 0.1 to 100 Gy per time over a period of one week to 6 months to give a total irradiation dose of about 10 to 500 Gy. Typical example of human radiotherapy is conducted by, not limited to, X ray irradiation with a dose of 2 Gy per time for five times thereby giving a total dose of 60 Gy over a period of about 6 weeks. For example, the dose and frequency of irradiation may be reduced. Other examples of the radiotherapy method include conformation radiotherapy, stereotactic irradiation wherein the focus of malignant neoplasm is shot with pinpoint precision, or intensity modulated radiotherapy. In addition, irradiation with encapsulated sealed radioactive source, γ ray teletherapy, or irradiation with particle beams also may be used. The irradiation dose per time may be increased, and the irradiation period may be reduced through internal irradiation.

Radiation therapy and administration of the radiosensitizer of the present invention may be conducted concurrently or sequentially. In this case, the radiosensitizer of the present invention is expected to serve as an antineoplastic agent to be combined with radiation therapy. Accordingly, according to another aspect of the present invention, the novel sulfoquinovosylacyl propanediol compound or pharmaceutically acceptable salts thereof according to the present invention may be provided as an antineoplastic agent to be combined with radiation therapy.

As known to those skilled in the field of radiotherapy treatment, the conditions of radiation therapy and administration of the radiosensitizer of the present invention may be appropriately selected by health professionals or other specialists depending on, for example: the type of radiation source, irradiation method, site and period of irradiation; type of sensitizer, route and timing of administration; type and seriousness of the disease to be treated; and age, body weight, health condition, and medical history of the subject to be exposed to radiation.

In addition, according to yet another aspect of the present invention, provided is a therapy for treating a disease against which radiation therapy is effective, including administration of an effective dose of the radiosensitizing substance to the subject in need of the substance. The term "a disease against which radiation therapy is effective" refers to a disease which is effectively treated by, for example, radiation therapy on the above-described malignant neoplasm. Details about the radiosensitizing substance and method and conditions of its administration may be as described above.

The therapy according to the present invention may include administration of an effective dose of the radiosensitizing substance to the subject in need of the substance, concurrently with radiation therapy, or before or after the radiation therapy.

According to yet another aspect of the present invention, the sulfoquinovosylacyl propanediol compound and pharmaceutically acceptable salts thereof have antineoplastic effect as a second pharmacological effect. More specifically, they synergistically accelerate the radiation effect, and can suppress malignant neoplasm when used alone. Accordingly, the sulfoquinovosylacyl propanediol compound and pharmaceutically acceptable salts thereof may be provided as an antineoplastic agent.

When the sulfoquinovosylacyl propanediol compound and pharmaceutically acceptable salts thereof are used as an antineoplastic agent, for example, they may be used in the same manner as the above-described radiosensitizer, except that they are not combined with radiation therapy.

In this case, the conditions for administering the sulfoquinovosylacyl propanediol compound (for example, dose, frequency of administration, and interval of administration) may be appropriately established and adjusted according to the dosage form, administration route, disease to be treated, for example, state of malignant neoplasm (for example, type, location, and stage), conditions such as the drug to be combined (for example, presence or absence of combined drug, type, dose, frequency, and timing of administration of combined drug, and sequence of administration of the combined drug and the radiosensitizing substance of the present invention), and the conditions of the subject to be treated (for example, body weight, sex, and age).

The various methods of treatment of the present invention may be applied to any subject in need thereof. Suitable subjects include but are not limited to mammals such as humans, chimpanzees, gorillas, monkeys, baboons, orangutans, dogs, cats, horses, cows, pigs, oxen, llamas, alpacas, bison, buffalo, camels, zebras, elephants, giraffes, hippopotami, bears, lions, tigers, leopards, antelope, etc. In a preferred embodiment the subject is a human.

Other features of the invention will become apparent in the course of the following descriptions of exemplary embodiments which are given for illustration of the invention and are not intended to be limiting thereof.

EXAMPLES

Example I

The steps for preparing the sulfoquinovosylacyl propanediol compound according to the present invention are described below taking, as an example, a sodium salt of α-sulfoquinovosyl stearoyl propanediol.

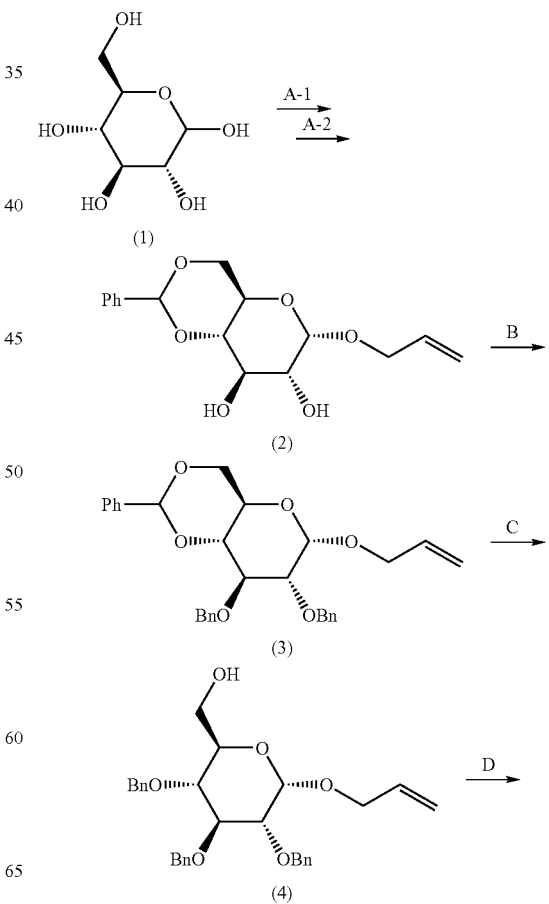

-continued

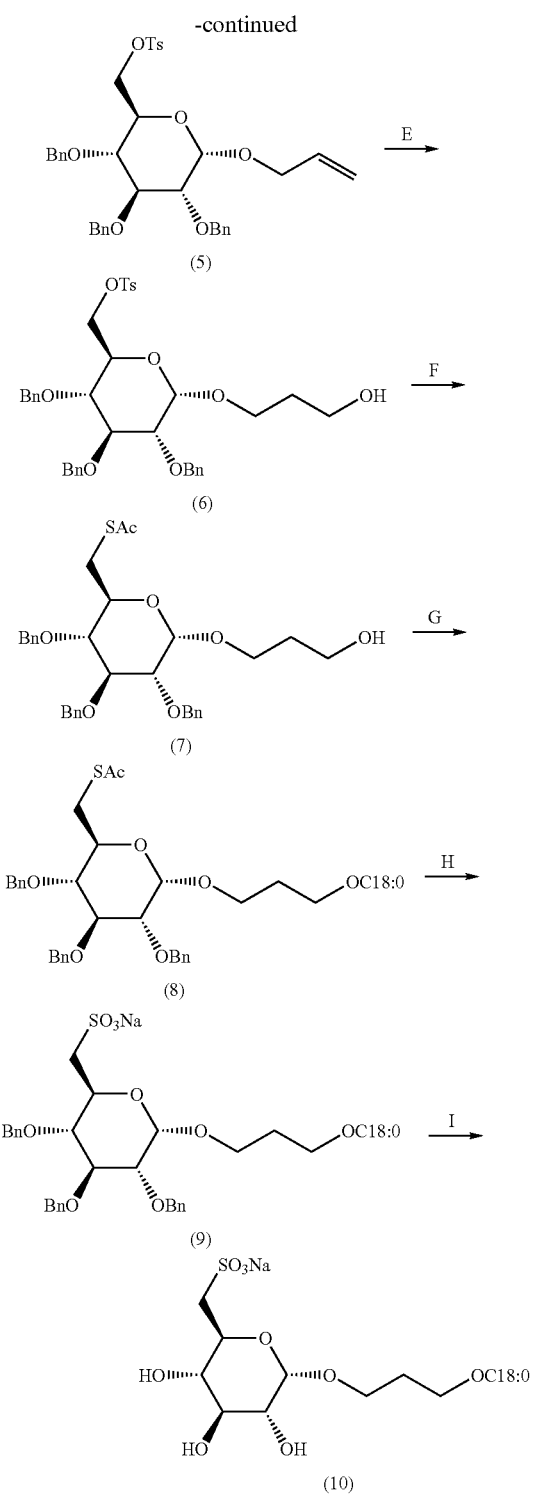

A) A-1. allyl alcohol, trifluoromethanesulfonic acid, 80° C., 48 hours;

A-2. benzaldehyde dimethyl acetal, p-toluene sulfonic acid monohydrate, acetonitrile, 40° C., 4 hours, 20.2%;

B) benzyl bromide, sodium hydroxide, N,N-dimethylformamide, room temperature, 24 hours, 84.4%;

C) lithium hydride aluminum, aluminum chloride, dichloromethane, diethyl ether, heating under reflux, 4 hours, 90.2%;

D) p-toluenesulfonyl chloride, 4-dimethylaminopyridine, pyridine, room temperature, 16 hours, 87.9%;

E) 9-borabicyclononane, tetrahydrofuran, room temperature, 10 hours; water, sodium hydroxide, hydrogen peroxide water, room temperature, 12 hours, 94.4%;

F) potassium thioacetate, N,N-dimethylformamide, 90° C., 3 hours, 90.8%;

G) stearoyl chloride, pyridine, dichloromethane, room temperature, 2 hours, 97.4%;

H) Oxone®, acetic acid, potassium acetate, room temperature, 48 hours, 88.6%; and I) palladium activated carbon, hydrogen gas, ethanol, dichloromethane, room temperature, 48 hours, 79.4%.

The procedure for obtaining, as the end product, a sodium salt of α-sulfoquinovosyl stearoyl propanediol according to an aspect of the present invention was conducted via the steps A to I in the above-described scheme.

Example I-1

Step A:
1-O-allyl-4,6-O-benzylidine-α-D-glucopyranose (2)

The compound (1) (100 g, 555 mmol) as the starting substance was suspended in allyl alcohol (500 ml), to which trifluoromethanesulfonic acid (1.00 ml) was added at 0° C., and the reaction liquid was vigorously stirred at 80° C. for 48 hours. After the sufficient progress of the reaction was confirmed, triethylamine (3 ml) was added to stop the reaction, and the reaction liquid was concentrated under reduced pressure. Subsequently, the residue was suspended in anhydrous acetonitrile (500 ml), to which benzaldehyde dimethyl acetal (127 g, 1.5 equivalent) and p-toluenesulfonic acid monohydrate (5.28 g, 0.05 equivalent) were added. The reaction liquid was stirred at 40° C. for 4 hours, to which triethylamine (10 ml) was added to stop the reaction, and the reaction liquid was concentrated under reduced pressure. The residue was poured to hexane (2000 ml) and water (500 ml), and the mixed liquid was vigorously stirred. The generated precipitate was collected by filtration, and rinsed with water and hexane. The precipitate was crystallized from heated ethanol twice to obtain the title compound (2) in the form of colorless needle crystals {34.5 g (112 mmol), 20.2%}.

$[\alpha]^{23}_D$ +97.5° (c1.00 CH$_3$OH), LRMS 331 m/z (M+Na)$^+$, mp 139-141° C.

$^1$H NMR (400 MHz, CD$_3$OD); δ 7.51-7.47 (m, 2H, ArH), 7.37-7.32 (m, 3H, ArH), 5.99 (dddd, 1H, J=17.2, 10.5, 6.08, 5.32 Hz, H2), 5.56 (s, 1H, PhCH), 5.36 (dq, 1H, J=17.3, 1.68 Hz, H3a), 5.20 (ddt, 1H, J=10.4, 1.80, 1.28 Hz, H3b), 4.88 (d, 1H, J=3.86 Hz, H1'), 4.25-4.18 (m, 2H, H1a & H6'a), 4.07 (ddt, 1H, J=13.0, 6.10, 1.36 Hz, H1b), 3.85 (t, 1H, J=9.38 Hz, H3'), 3.81-3.71 (m, 2H, H5' & H6'b), 3.52 (dd, 1H, J=9.38, 3.86 Hz, H2'), 3.45 (t, 1H, J=9.24 Hz, H4').

$^{13}$C NMR (100 MHz, CD$_3$OD); δ 139.1 (Ar-ipso), 135.4 (C2), 129.9 (Ar), 129.0 (Ar), 127.5 (Ar), 117.8 (C3), 103.0 (PhCH), 100.0 (C1'), 82.9 (C4'), 74.0 (C2'), 72.0 (C3'), 69.9 (C6'), 69.7 (C1), 64.1 (C5).

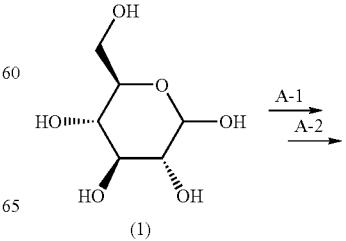

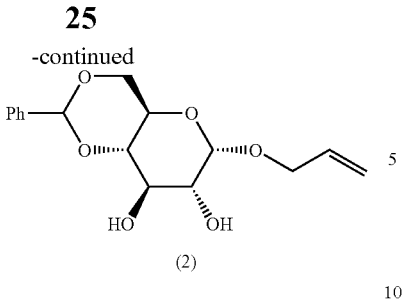

(2)

Example I-2

Step B; 1-O-allyl-2,3-di-O-benzyl-4,6-O-benzylidene-α-D-glucopyranose (3)

To a solution of the compound (2) (30.0 g, 97.3 mmol) in anhydrous N,N-dimethylformamide (DMF, 300 ml) were added benzyl bromide (41.6 g, 2.5 equivalents) and sodium hydroxide (11.7 g, 3.0 equivalents), and the reaction liquid was vigorously stirred at room temperature for 24 hours. After the sufficient progress of the reaction was confirmed, the reaction liquid was poured to chilled water (900 ml), and extracted with ethyl acetate (3×300 ml). The organic layers were combined and washed with saturated saline (2×100 ml), dried with sodium sulfate, filtered, concentrated under reduced pressure. The obtained residue was crystallized twice from heated ethanol to obtain the title compound (3) in the form of colorless needle crystals (33.5 g). The filtrate was concentrated, purified with silica gel chromatography (hexane-ethyl acetate, 15:1→10:1→8:1), crystallized from heated ethanol to obtain the compound (3) (6.63 g) {40.1 g (82.1 mmol) in total, 84.4%}.

$[\alpha]^{26}_D$ −1.46° (c1.03 CHCl$_3$), LRMS 511 m/z (M+Na)$^+$, mp 86-87° C.

$^1$H NMR (400 MHz, CDCl$_3$); δ 7.50-7.47 (m, 2H, ArH), 7.40-7.24 (m, 13H, ArH), 5.94 (dddd, 1H, J=17.0, 10.4, 6.70, 5.24 Hz, H2), 5.56 (s, 1H, PhCH), 5.33 (dq, 1H, J=17.2, 1.56 Hz, H3a), 5.24 (ddt, 1H, J=10.3, 1.56, 1.12 Hz, H3b), 4.92 (d, 1H, J=11.2 Hz, ArCH$_2$), 4.84 (d, 1H, J=11.2 Hz, ArCH$_2$), 4.83 (d, 1H, J=12.1 Hz, ArCH$_2$), 4.80 (d, 1H, J=3.76 Hz, H1'), 4.68 (d, 1H, J=12.1 Hz, ArCH$_2$), 4.26 (dd, 1H, J=10.2, 4.84 Hz, H6'a), 4.18 (ddt, 1H, J=12.9, 5.18, 1.40 Hz, H1a), 4.79 (t, 1H, J=9.30 Hz, H3'), 4.03 (ddt, 1H, J=12.9, 6.68, 1.20 Hz, H1b), 3.89 (dt, 1H, J=9.96, 4.80 Hz, H5'), 3.70 (t, 1H, J=10.3 Hz, H6'b), 3.61 (t, 1H, J=9.44 Hz, H4'), 3.57 (dd, 1H, J=8.72, 3.80 Hz, H2').

$^{13}$C NMR (100 MHz, CDCl$_3$); δ 138.7 (Ar-ipso), 138.1 (Ar-ipso), 137.3 (Ar-ipso), 133.5 (C2), 128.9-127.5 (m, Ar), 126.0 (Ar), 118.4 (C3), 101.2 (PhCH), 96.7 (C1'), 82.1 (C3'), 79.1 (C2'), 78.6 (C4'), 75.3 (ArCH$_2$), 73.6 (ArCH$_2$), 69.0 (C6'), 68.4 (C1), 62.5 (C5').

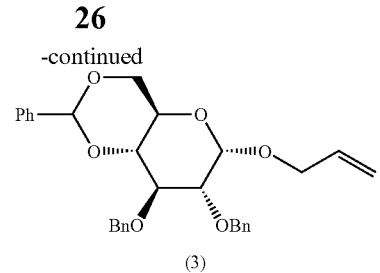

(3)

Example I-3

Step C; 1-O-allyl-2,3,4-tri-O-benzyl-α-D-glucopyranose (4)

Aluminum lithium hydride (2.02 g, 1.3 equivalents) is suspended in a mixed solution of anhydrous dichloromethane (100 ml) and anhydrous diethyl ether (100 ml), to which the compound (3) (20.0 g, 40.9 mmol) was added. Subsequently, to the reaction liquid, added was 200 ml of an aluminum chloride (7.09 g, 1.3 equivalents) solution in anhydrous diethyl ether, and the mixture was stirred for 4 hours under heating and reflux. After the sufficient progress of the reaction was confirmed, water (10 ml) was slowly added dropwise, the precipitate was collected by filtration after standing overnight, and then the precipitate was rinsed with diethyl ether. The filtrate was washed with water (2×100 ml), the aqueous layers were combined, and extracted with diethyl ether (2×100 ml). The organic layers were combined and washed with saturated saline (2×200 ml), dried with sodium sulfate, filtered, and concentrated under reduced pressure. The obtained residue was purified with silica gel chromatography (hexane-ethyl acetate, 5:1→4:1→3:1→2:1) to obtain the title compound (4) in the form of a colorless oily substance {18.1 g (36.9 mmol), 90.2%}.

$[\alpha]^{22}_D$ +45.0° (c1.21 CHCl$_3$), LRMS m/z 513 (M+Na)$^+$.

$^1$H NMR (400 MHz, CDCl$_3$); δ 7.37-7.26 (m, 15H, ArH), 5.92 (dddd, 1H, J=17.1, 10.4, 6.66, 5.24 Hz, H2), 5.31 (dq, 1H, J=17.2, 1.52 Hz, H3a), 5.22 (ddt, 1H, J=10.3, 1.46, 1.10 Hz, H3b), 5.00 (d, 1H, J=10.9 Hz, ArCH$_2$), 4.89 (d, 1H, J=11.0 Hz, ArCH$_2$), 4.84 (d, 1H, J=10.9 Hz, ArCH$_2$), 4.77 (d, 1H, J=12.0 Hz, ArCH$_2$), 4.77 (d, 1H, J=3.60 Hz, H1'), 4.65 (d, 1H, J=12.1 Hz, ArCH$_2$), 4.64 (d, 1H, J=11.0 Hz, ArCH$_2$), 4.14 (ddt, 1H, J=12.9, 5.22, 1.34 Hz, H1a), 4.04 (t, 1H, J=9.36 Hz, H3'), 3.99 (ddt, 1H, J=12.9, 6.64, 1.08 Hz, H1b), 3.79-3.66 (m, 3H, H5' & H6'a & H6'b), 3.54 (t, 1H, J=9.28 Hz, H4'), 3.51 (dd, 1H, J=9.60, 3.64 Hz, H2'), 1.69 (t, 1H, J=12.0 Hz, 6'-OH).

$^{13}$C NMR (100 MHz, CDCl$_3$); δ 138.7 (Ar-ipso), 138.1 (Ar-ipso), 138.1 (Ar-ipso), 133.6 (C2), 128.4-127.6 (m, Ar), 118.3 (C3), 95.6 (C1'), 81.9 (C3'), 79.9 (C2'), 77.3 (C4'), 75.7 (ArCH$_2$), 75.0 (ArCH$_2$), 73.2 (ArCH$_2$), 70.8 (C5'), 68.2 (C1), 61.7 (C6').

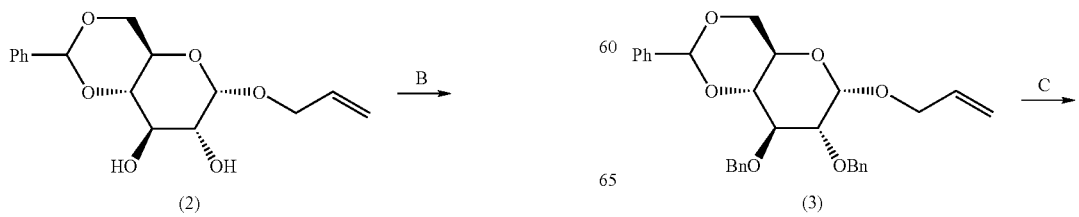

-continued

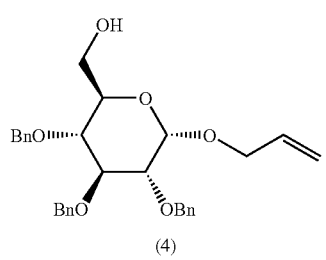

(4)

Example I-4

Step D; 1-O-allyl-2,3,4-tri-O-benzyl-6-O-tosyl-α-D-glucopyranose (5)

To a solution of the compound (4) (25.1 g, 51.2 mmol) in anhydrous pyridine (250 ml) were added p-toluenesulfonyl chloride (14.6 g, 1.5 equivalents) and 4-dimethylaminopyridine (626 mg, 0.1 equivalents), and the reaction liquid was stirred at room temperature for 16 hours. After the sufficient progress of the reaction was confirmed, water (10 ml) was added to stop the reaction, and the reaction liquid was concentrated under reduced pressure. The residue was suspended in a minor amount of ethyl acetate, poured to 0.5 M hydrochloric acid (200 ml), and extracted with ethyl acetate (3×200 ml). The organic layers were combined, washed with a saturated sodium hydrogen carbonate solution (2×100 ml) and saturated saline (2×100 ml), dried with sodium sulfate, filtered, and concentrated under reduced pressure. The obtained residue was crystallized twice from heated ethanol to obtain the title compound (5) in the form of colorless needle crystals (25.0 g). The filtrate was concentrated, purified with silica gel chromatography (hexane-ethyl acetate, 5:1→4:1→3:1) to obtain the compound (5) (4.00 g). {29.0 g (45.0 mmol) in total, 87.9%}.

$[\alpha]^{25}_D$ +32.1° (c1.02 CHCl$_3$), LRMS 667 m/z (M+Na)$^+$, mp 86-87° C.

$^1$H NMR (400 MHz, CDCl$_3$); δ 7.76 (ddd, 2H, J=8.32, 1.96, 1.76 Hz, ArH), 7.35-7.26 (m, 15H, ArH), 7.17-7.12 (m, 2H, ArH), 5.88 (dddd, 1H, J=17.2, 10.3, 6.62, 5.24 Hz, H2), 5.28 (dq, 1H, J=17.2, 1.56 Hz, H3a), 5.20 (ddt, 1H, J=10.3, 1.60, 1.12 Hz, H3b), 4.99 (d, 1H, J=10.9 Hz, ArCH$_2$), 4.82 (d, 1H, J=10.6 Hz, ArCH$_2$), 4.78 (d, 1H, J=10.8 Hz, ArCH$_2$), 4.74 (d, 1H, J=12.1 Hz, ArCH$_2$), 4.72 (d, 1H, J=3.58 Hz, H1'), 4.62 (d, 1H, J=12.1 Hz, ArCH$_2$), 4.42 (d, 1H, J=10.6 Hz, ArCH$_2$), 4.22 (dd, 1H, J=10.5, 4.20 Hz, H6'a), 4.16 (dd, 1H, J=10.5, 2.12 Hz, H6'b), 4.07 (ddt, 1H, J=12.9, 5.24, 1.40 Hz, H1a), 3.98 (t, 1H, J=9.24 Hz, H3'), 3.93 (ddt, 1H, J=12.9, 6.64, 1.16 Hz, H1b), 3.81 (dddd, 1H, J=10.1, 4.12, 2.04 Hz, H5'), 3.48 (dd, 1H, J=9.62, 3.58 Hz, H2'), 3.45 (dd, 1H, J=10.0, 8.90 Hz, H4'), 2.39 (s, 3H, Ts-Me).

$^{13}$C NMR (100 MHz, CDCl$_3$); δ 144.8 (Ar-ipso), 138.5 (Ar-ipso), 137.9 (Ar-ipso), 137.7 (Ar-ipso), 133.4 (C2), 132.8 (Ar-ipso), 129.8 (Ar), 128.4-127.6 (m, Ar), 118.4 (C3), 95.4 (C1'), 81.8 (C3'), 79.6 (C2'), 76.9 (C4'), 75.7 (ArCH$_2$), 75.0 (ArCH$_2$), 73.2 (ArCH$_2$), 68.6 (C5'), 68.5 (C6'), 68.3 (C1), 21.6 (Ts-Me).

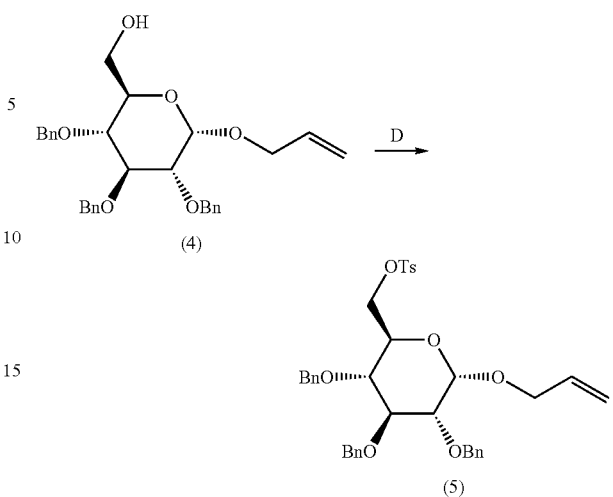

Example I-5

Step E; 1-O-(2,3,4-tri-O-benzyl-6-O-tosyl-α-D-glucopyranosyl)-propane-1,3-diol (6)

To a solution of the compound (5) (29.0 g, 45.0 mmol) in anhydrous tetrahydrofuran (THF, 150 ml), added was a solution of 0.5 M 9-borabicyclo[3,3,1]nonane (9-BBN) in tetrahydrofuran (180 ml, 90.0 mmol) at 0° C. in an argon atmosphere. After a lapse of 1 hour, the reaction liquid was returned to room temperature, and continuously stirred for 10 hours. The reaction liquid was cooled again to 0° C., to which water (20 ml) was added firstly, and then 3 M sodium hydroxide solution (70 ml) and 35% hydrogen peroxide solution (70 ml) were added sequentially. After a lapse of 1 hour, the reaction liquid was returned to room temperature, and stirred for 12 hours. After the sufficient progress of the reaction was confirmed, the solution was extracted with ethyl acetate (3×100 ml), the organic layers were combined and washed with saturated saline (2×100 ml), dried with sodium sulfate, filtered, and concentrated under reduced pressure. The obtained residue was purified with silica gel chromatography (hexane-ethyl acetate, 3:2→1:1→2:3) to obtain the title compound (6) in the form of a colorless oily substance {28.2 g (42.5 mmol), 94.4%}.

$[\alpha]^{24}_D$ +26.6° (c1.02 CHCl$_3$), LRMS m/z 685 (M+Na)$^+$.

$^1$H NMR (400 MHz, CDCl$_3$); δ 7.76-7.74 (m, 2H, ArH), 7.35-7.26 (m, 15H, ArH), 7.16-7.12 (m, 2H, ArH), 4.94 (d, 1H, J=10.9 Hz, ArCH$_2$), 4.82 (d, 1H, J=10.7 Hz, ArCH$_2$), 4.77 (d, 1H, J=10.9 Hz, ArCH$_2$), 4.75 (d, 1H, J=12.0 Hz, ArCH$_2$), 4.61 (d, 1H, J=12.0 Hz, ArCH$_2$), 4.61 (d, 1H, J=3.64 Hz, H1'), 4.43 (d, 1H, J=10.7 Hz, ArCH$_2$), 4.20-4.13 (m, 2H, H6'a & H6'b), 3.92 (t, 1H, J=9.24 Hz, H3'), 3.84-3.74 (m, 4H, H1a & H3a & H3b & H5'), 3.48-3.40 (m, 3H, H1b & H2' & H4'), 2.52 (t, 1H, J=4.74 Hz, 3-OH), 2.39 (s, 3H, Ts-Me), 1.88-1.75 (m, 2H, H2a & H2b).

$^{13}$C NMR (100 MHz, CDCl$_3$); δ 144.8 (Ar-ipso), 138.4 (Ar-ipso), 137.9 (Ar-ipso), 137.6 (Ar-ipso), 132.7 (Ar-ipso), 129.8 (Ar), 128.5-127.6 (m, Ar), 97.1 (C1'), 81.8 (C3'), 79.5 (C2'), 76.8 (C4'), 75.6 (ArCH$_2$), 75.0 (ArCH$_2$), 73.4 (ArCH$_2$), 68.7 (C5'), 68.6 (C6'), 67.5 (C1), 61.5 (C3), 31.5 (C2), 21.6 (Ts-Me).

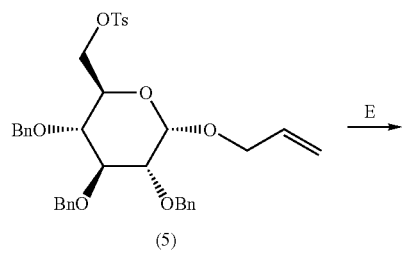

(5)

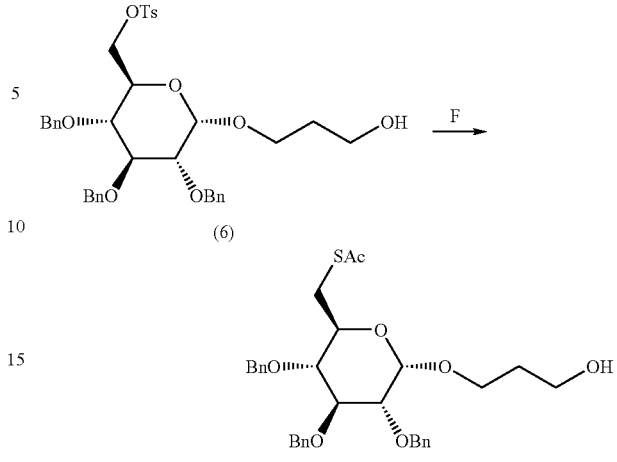

(6)

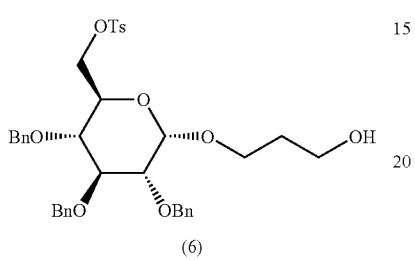

(6)

(7)

Example I-6

Step F; 1-O-(2,3,4-tri-O-benzyl-6-thioacetyl-α-D-quinovopyranosyl)-propane-1,3-diol (7)

To a solution of the compound (6) (28.2 g, 42.5 mmol) in anhydrous DMF (300 ml), added was potassium thioacetate (7.28 g, 1.5 equivalents), and the mixture was stirred at 90° C. for 3 hours. After the sufficient progress of the reaction was confirmed, the reaction liquid was poured to chilled water (900 ml), extracted with ethyl acetate (3×300 ml). The organic layers were combined and washed with saturated saline (2×200 ml), dried with sodium sulfate, filtered, and concentrated under reduced pressure. The obtained residue was purified with silica gel chromatography (hexane-ethyl acetate, 2:1→3:2→1:1→2:3) to obtain the title compound (7) in the form of light brown oily substance {21.9 g (38.6 mmol), 90.8%}.

$[\alpha]^{23}_D$ +33.0° (c1.02 CHCl$_3$), LRMS 584 m/z (M+Na)$^+$.

$^1$H NMR (400 MHz, CDCl$_3$); δ 7.37-7.24 (m, 15H, ArH), 4.95 (d, 1H, J=10.8 Hz, ArCH$_2$), 4.89 (d, 1H, J=10.6 Hz, ArCH$_2$), 4.80 (d, 1H, J=10.8 Hz, ArCH$_2$), 4.77 (d, 1H, J=12.1 Hz, ArCH$_2$), 4.63 (d, 1H, J=12.0 Hz, ArCH$_2$), 4.63 (d, 1H, J=3.52 Hz, H1'), 4.61 (d, 1H, J=10.7 Hz, ArCH$_2$), 3.94 (t, 1H, J=9.22 Hz, H3'), 3.88 (ddd, 1H, J=9.86, 6.10, 4.88 Hz, H1a), 3.83-3.73 (m, 3H, H3a & H3b & H5'), 3.50 (dd, 1H, J=9.60, 3.64 Hz, H2'), 3.45 (ddd, 1H, J=9.92, 5.24, 2.28 Hz, H1b), 3.41 (dd, 1H, J=13.6, 3.00 Hz, H6'a), 3.30 (dd, 1H, J=9.54, 9.06 Hz, H4'), 3.02 (dd, 1H, J=13.7, 7.64 Hz, H6'b), 2.67 (br, 1H, 3-OH), 2.32 (s, 3H, SAc-Me), 1.92-1.78 (m, 2H, H2a & H2b).

$^{13}$C NMR (100 MHz, CDCl$_3$); δ 195.0 (SAc—C═O), 138.5 (Ar-ipso), 137.9 (Ar-ipso), 137.8 (Ar-ipso), 128.5-127.6 (m, Ar), 96.9 (C1'), 81.8 (C3'), 80.4 (C4'), 79.8 (C2'), 75.7 (ArCH$_2$), 75.2 (ArCH$_2$), 73.4 (ArCH$_2$), 69.5 (C5'), 67.2 (C1), 61.5 (C3), 31.5 (C2), 30.8 (C6'), 30.5 (SAc-Me).

Example I-7

Step G; 3-O-(2,3,4-tri-O-benzyl-6-thio acetyl-α-D-quinovopyranosyl)-1-O-stearoyl-propane-1,3-diol (8)

To a solution of the compound (7) (21.9 g, 38.6 mmol) in anhydrous dichloromethane (200 ml), added were stearoyl chloride (15.2 g, 1.3 equivalents) and anhydrous pyridine (5 ml), and the mixture was stirred at room temperature for 2 hours. After the sufficient progress of the reaction was confirmed, methanol (5 ml) was added to stop the reaction, and the mixture was concentrated under reduced pressure. The residue was suspended in a minor amount of ethyl acetate, poured to water (200 ml), and extracted with ethyl acetate (3×100 ml). The organic layers were combined and washed with saturated saline (2×100 ml), dried with sodium sulfate, filtered, and concentrated under reduced pressure. The obtained residue was purified with silica gel chromatography (hexane-ethyl acetate, 10:1→8:1→6:1) to obtain the title compound (8) in the form of a colorless oily substance {31.3 g (37.6 mmol), 97.4%}.

$[\alpha]^{23}_D$ +29.5° (c1.01 CHCl$_3$), LRMS m/z 855 (M+Na)$^+$.

$^1$H NMR (400 MHz, CDCl$_3$); δ 7.35-7.25 (m, 15H, ArH), 4.98 (d, 1H, J=10.8 Hz, ArCH$_2$), 4.89 (d, 1H, J=10.6 Hz, ArCH$_2$), 4.80 (d, 1H, J=10.8 Hz, ArCH$_2$), 4.76 (d, 1H, J=12.0 Hz, ArCH$_2$), 4.66 (d, 1H, J=3.60 Hz, H1'), 4.63 (d, 1H, J=12.1 Hz, ArCH$_2$), 4.62 (d, 1H, J=10.7 Hz, ArCH$_2$), 4.23-4.14 (m, 2H, H1a & H1b), 3.96 (t, 1H, J=9.20 Hz, H3'), 3.78 (ddd, 1H, J=9.68, 7.56, 2.92 Hz, H5'), 3.72 (dt, 1H, J=10.0, 6.40 Hz, H3a), 3.50 (dd, 1H, J=9.64, 3.60 Hz, H2'), 3.43 (dt, 1H, J=9.72, 6.36 Hz, H3b), 3.41 (dd, 1H, J=13.6, 2.96 Hz, H6'a), 3.31 (t, 1H, J=9.24 Hz, H4'), 3.05 (dd, 1H, J=13.6, 7.56 Hz, H6'b), 2.33 (s, 3H, SAc-Me), 2.29 (t, 2H, J=7.68 Hz, COCH$_2$), 1.95 (f, 2H, J=6.40 Hz, H2a & H2b), 1.61 (f, 2H, J=7.24 Hz, COCH$_2$CH$_2$), 1.25 (br, 28H, —CH$_2$—), 0.88 (t, 3H, J=6.84 Hz, Me).

$^{13}$C NMR (100 MHz, CDCl$_3$); δ 194.8 (SAc—C═O), 173.8 (C═O), 138.6 (Ar-ipso), 138.1 (Ar-ipso), 137.8 (Ar-ipso), 128.4-127.6 (m, Ar), 96.8 (C1'), 81.7 (C3'), 80.4 (C4'), 80.1 (C2'), 75.7 (ArCH$_2$), 75.2 (ArCH$_2$), 73.2 (ArCH$_2$), 69.4 (C5'), 64.6 (C3), 61.2 (C1), 34.3 (COCH$_2$), 31.9 (—CH$_2$—), 30.9 (C6'), 30.5 (SAc-Me), 29.7-29.2 (m, —CH$_2$—), 28.7 (C2), 25.0 (COCH$_2$CH$_2$), 22.7 (—CH$_2$—), 14.1 (Me).

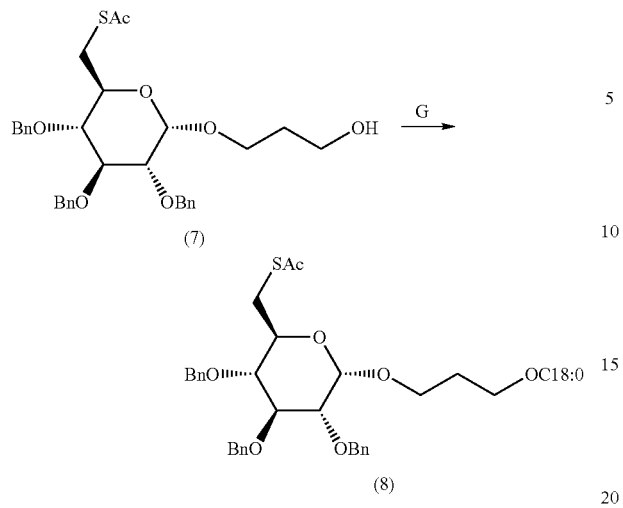
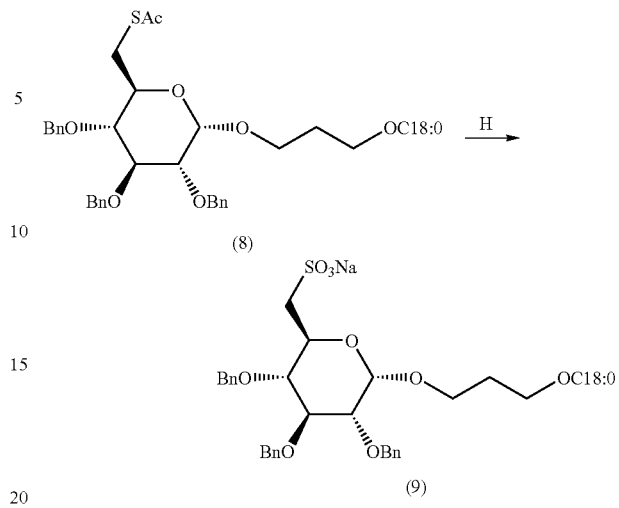

Example I-8

Step H; 3-O-(2,3,4-tri-O-benzyl-6-sulfo-α-D-quinovopyranosyl)-1-O-stearoyl-propane-1,3-diol sodium salt (9)

To a solution of the compound (8) (31.3 g, 37.6 mmol) in acetic acid (450 ml) were added Oxone® (46.2 g) and potassium acetate (11.3 g), and the mixture was vigorously stirred at room temperature 48 hours. After the sufficient progress of the reaction was confirmed, the reaction liquid was poured to a chilled 7.5 M sodium hydroxide solution (1000 ml), and extracted with ethyl acetate (4×200 ml). The organic layers were combined, washed with saturated sodium hydrogen carbonate solution (2×200 ml) and saturated saline (2×200 ml), dried with sodium sulfate, filtered, and concentrated under reduced pressure. The obtained residue was purified with silica gel chromatography (dichloromethane-methanol, 15:1→10:1→8:1) to obtain the title compound (9) in the form of a colorless waxy substance {28.7 g (33.3 mmol), 88.6%}.

$[\alpha]^{23}_D$ +29.0° (c1.16 CHCl$_3$), LRMS m/z 837 (M−Na)$^-$.

$^1$H NMR (400 MHz, DMSO-d$_6$); δ 7.36-7.22 (m, 15H, ArH), 4.85 (d, 1H, J=11.2 Hz, ArCH$_2$), 4.81 (d, 1H, J=3.72 Hz, H1'), 4.79 (d, 1H, J=11.4 Hz, ArCH$_2$), 4.69 (d, 1H, J=11.2 Hz, ArCH$_2$), 4.65 (d, 1H, J=12.0 Hz, ArCH$_2$), 4.61 (d, 1H, J=12.0 Hz, ArCH$_2$), 4.58 (d, 1H, J=11.4 Hz, ArCH$_2$), 4.19-4.10 (m, 2H, H1a & H1b), 4.05-3.96 (m, 2H, H3a & H5'), 3.79 (t, 1H, J=9.14 Hz, H3'), 3.47 (dd, 1H, J=9.56, 3.60 Hz, H2'), 3.38 (dt, 1H, J=10.1, 6.20 Hz, H3b), 3.20 (dd, 1H, J=9.80, 9.00 Hz, H4'), 2.94 (dd, 1H, J=13.9, 1.16 Hz, H6'a), 2.63 (dd, 1H, J=14.0, 9.06 Hz, H6'b), 2.29 (t, 2H, J=7.38 Hz, COCH$_2$), 1.86 (f, 2H, J=6.36 Hz, H2a & H2b), 1.52 (f, 2H, J=7.12 Hz, COCH$_2$CH$_2$), 1.23 (br, 28H, —CH$_2$—), 0.85 (t, 3H, J=6.84 Hz, Me).

$^{13}$C NMR (100 MHz, DMSO-d$_6$); δ 172.9 (C=O), 138.9 (Ar-ipso), 138.6 (Ar-ipso), 138.6 (Ar-ipso), 128.2-127.3 (m, Ar), 95.0 (C1'), 81.4 (C3'), 80.5 (C4'), 80.0 (C2'), 74.4 (ArCH$_2$), 73.7 (ArCH$_2$), 71.4 (ArCH$_2$), 67.3 (C5'), 63.4 (C3), 61.5 (C1), 52.8 (C6'), 33.6 (COCH$_2$), 31.3 (—CH$_2$—), 29.0-28.4 (m, C2 & —CH$_2$—), 24.5 (COCH$_2$CH$_2$), 22.1 (—CH$_2$—), 13.9 (Me).

Example I-9

Step I; 3-O-(6-sulfo-α-D-quinovopyranosyl)-1-O-stearoyl-propane-1,3-diol sodium salt (10)

To a solution of the compound (9) (28.7 g, 33.3 mmol) in ethanol (400 ml) and dichloromethane (150 ml) was added 10% palladium activated carbon (7.00 g), and the mixture was stirred at room temperature for 48 hours in a hydrogen gas atmosphere. After the sufficient progress of the reaction was confirmed, palladium activated carbon was removed by filtration, and the filtrate was concentrated under reduced pressure. The obtained residue was purified with silica gel chromatography (dichloromethane-methanol, 10:1→5:1→3:1→2:1→1:1), and precipitated from 98% heated ethanol to obtain the title compound (10) in the form of a colorless powder {15.6 g (26.4 mmol), 79.4%}.

$[\alpha]^{22}_D$ +49.6° (c1.00 H$_2$O), LRMS m/z 567 (M−Na)$^-$, HRMS calcd for C$_{27}$H$_{51}$O$_{10}$S (M−Na)$^-$ 567.3208. found 567.3210.

$^1$H NMR (400 MHz, DMSO-d$_6$); δ 5.40 (d, 1H, J=3.48 Hz, 4'-OH), 4.58 (d, 1H, J=4.64 Hz, 3'-OH), 4.56 (d, 1H, J=3.72 Hz, H1'), 4.45 (d, 1H, J=6.52 Hz, 2'-OH), 4.15-4.06 (m, 2H, H1a & H1b), 3.84-3.78 (m, 2H, H3a & H5'), 3.42-3.34 (m, 2H, H3b & H3'), 3.19 (ddd, 1H, J=9.62, 6.50, 3.76 Hz, H2'), 2.98-2.91 (m, 2H, H4' & H6'a), 2.63 (dd, 1H, J=14.0, 6.00 Hz, H6'b), 2.28 (t, 2H, J=7.40 Hz, COCH$_2$), 1.86-1.80 (m, 2H, H2a & H2b), 1.55-1.48 (m, 2H, COCH$_2$CH$_2$), 1.24 (br, 28H, —CH$_2$—), 0.86 (t, 3H, J=6.84 Hz, Me).

$^{13}$C NMR (100 MHz, DMSO-d$_6$); δ 172.8 (C=O), 98.2 (C1'), 74.7 (C4'), 73.1 (C3'), 71.8 (C2'), 68.2 (C5'), 63.4 (C3), 61.2 (C1), 55.1 (C6'), 33.4 (COCH$_2$), 31.2 (—CH$_2$—), 28.9-28.4 (m, C2 & —CH$_2$—), 24.4 (COCH$_2$CH$_2$), 22.0 (—CH$_2$—), 13.8 (Me).

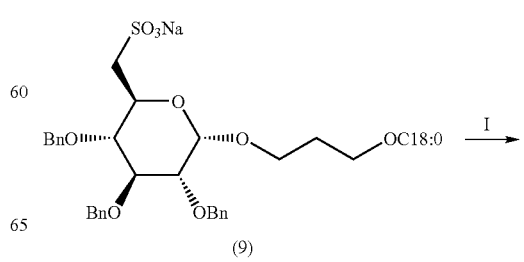

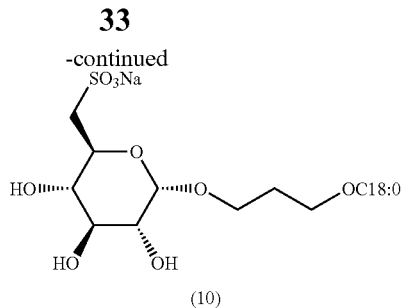

(10)

2.15 g of 3-O-(6-sulfo-α-D-quinovopyranosyl)-1-O-stearoyl-propane-1,3-diol sodium salt was dissolved in 60 ml of water, adsorbed to a WAKOGEL® 100C18 (manufactured by Wako Pure Chemical Industries, Ltd.) column, and 500 ml of 1% calcium chloride solution was poured into the column for substitution, and washed with 500 ml of distilled water. Thereafter, elution was performed with 200 ml each of 50%, 80%, and 100% methanol, and reprecipitated from 98% heated ethanol to obtain 1.47 g of 3-O-(6-sulfo-α-D-quinovopyranosyl)-1-O-stearoyl-propane-1,3-diol calcium salt.

Although not shown in Examples, with the same column treatment, a magnesium or potassium salt can be obtained through substitution with a magnesium chloride or potassium chloride solution.

Example II

As other examples of α-sulfoquinovosylacyl propanediol compounds, described below are the α anomer compounds having 22, 14, 10, 6, 2, and 1 carbon atoms within the acyl residue of the fatty acid.

Example II-1

3-O-(6-sulfo-α-D-quinovopyranosyl)-1-O-decanoyl-propane-1,3-diol sodium salt

The title compound was synthesized in the same manner as Example I, except that decanoyl chloride was used as the fatty acid derivative in the step G.

$[\alpha]^{22}_D$ +57.9° (c 0.76, $H_2O$), LRMS m/z 455 (M−Na)$^-$, HRMS calcd for $C_{19}H_{35}O_{10}S$ (M−Na)$^-$ 455.1956. found 455.1954.

$^1$H NMR (400 MHz, DMSO-$d_6$); δ 5.40 (d, 1H, J=3.1 Hz, 4'-OH), 4.65 (d, 1H, J=4.7 Hz, 3'-OH), 4.56 (d, 1H, J=3.7 Hz, H1'), 4.52 (d, 1H, J=6.48 Hz, 2'-OH), 4.14-4.08 (m, 2H, H1a & H1b), 3.84-3.78 (m, 2H, H3a & H5'), 3.41-3.33 (m, 2H, H3b & H3'), 3.21-3.16 (m, 1H, H2'), 2.97-2.92 (m, 2H, H4' & H6'a), 2.61 (dd, 1H, J=14.0, 6.2 Hz, H6'b), 2.29 (t, 2H, J=7.4 Hz, $COCH_2$), 1.84-1.81 (m, 2H, H2a & H2b), 1.53-1.50 (m, 2H, $COCH_2CH_2$), 1.25 (br, 12H, —$CH_2$—), 0.86 (t, 3H, J=6.8 Hz, Me).

$^{13}$C NMR (100 MHz, DMSO-$d_6$); δ 173.1 (C=O), 98.4 (C1'), 74.8 (C4'), 73.2 (C3'), 71.9 (C2'), 68.4 (C5'), 63.5 (C3), 61.4 (C1), 55.2 (C6'), 33.6 ($COCH_2$), 31.4 (—$CH_2$—), 29.0-28.6 (m, C2 & —$CH_2$—), 24.6 ($COCH_2CH_2$), 22.2 (—$CH_2$—), 14.1 (Me).

Example II-2

3-O-(6-sulfo-α-D-quinovopyranosyl)-1-O-myristoyl-propane-1,3-diol sodium salt

The title compound was synthesized in the same manner as Example I, except that myristoyl chloride was used as the fatty acid derivative in the step G.

$[\alpha]^{23}_D$ +49.7° (c 0.67, $H_2O$), LRMS m/z 511 (M−Na)$^-$, HRMS calcd for $C_{23}H_{43}O_{10}S$ (M−Na)$^-$ 511.2582. found 511.2596.

$^1$H NMR (400 MHz, DMSO-$d_6$); δ 5.41 (br, 1H, 4'-OH), 4.63-4.61 (m, 1H, 3'-OH), 4.55 (d, 1H, J=3.7 Hz, H1'), 4.50-4.48 (m, 1H, 2'-OH), 4.13-4.07 (m, 2H, H1a & H1b), 3.83-3.77 (m, 2H, H3a & H5'), 3.41-3.33 (m, 2H, H3b & H3'), 3.20-3.15 (m, 1H, H2'), 2.98-2.91 (m, 2H, H4' & H6'a), 2.64-2.59 (m, 1H, H6'b), 2.28 (t, 2H, J=7.4 Hz, $COCH_2$), 1.86-1.79 (m, 2H, H2a & H2b), 1.53-1.49 (m, 2H, $COCH_2CH_2$), 1.24 (br, 20H, —$CH_2$—), 0.85 (t, 3H, J=6.8 Hz, Me).

$^{13}$C NMR (100 MHz, DMSO-$d_6$); δ 173.0 (C=O), 98.4 (C1'), 74.8 (C4'), 73.2 (C3'), 71.9 (C2'), 68.4 (C5'), 63.5 (C3), 61.4 (C1), 55.3 (C6'), 33.6 ($COCH_2$), 31.4 (—$CH_2$—), 29.1-28.6 (m, C2 & —$CH_2$—), 24.6 ($COCH_2CH_2$), 22.2 (—$CH_2$—), 14.0 (Me).

Example II-3

3-O-(6-sulfo-α-D-quinovopyranosyl)-1-O-behenoyl-propane-1,3-diol sodium salt

The title compound was synthesized in the same manner as Example I, except that behenoyl chloride was used as the fatty acid derivative in the step G.

$[\alpha]^{23}_D$ +46.3° (c 0.51, $CHCl_3$:MeOH:$H_2O$=30:15:2), LRMS m/z 623 (M−Na)$^-$, HRMS calcd for $C_{21}H_{59}O_{10}S$ (M−Na)$^-$ 623.3834. found 623.3835.

$^1$H NMR (400 MHz, DMSO-$d_6$); δ 5.38-5.37 (m, 1H, 4'-OH), 4.78-4.77 (m, 1H, 3'-OH), 4.63 (d, 1H, J=6.52 Hz, 2'-OH), 4.56 (d, 1H, J=3.72 Hz, H1'), 4.14-4.07 (m, 2H, H1a & H1b), 3.86-3.78 (m, 2H, H3a & H5'), 3.43-3.32 (m, 2H, H3b & H3'), 3.22-3.17 (m, 1H, H2'), 2.98-2.90 (m, 2H, H4' & H6'a), 2.60 (dd, 1H, J=14.0, 6.7 Hz, H6'b), 2.28 (t, 2H, J=7.22 Hz, $COCH_2$), 1.86-1.79 (m, 2H, H2a & H2b), 1.52-1.49 (m, 2H, $COCH_2CH_2$), 1.23 (br, 36H, —$CH_2$—), 0.85 (t, 3H, J=6.1 Hz, Me).

$^{13}$C NMR (100 MHz, DMSO-$d_6$); δ 173.4 (C=O), 98.5 (C1'), 74.7 (C4'), 73.2 (C3'), 72.2 (C2'), 68.6 (C5'), 63.6 (C3), 61.8 (C1), 55.0 (C6'), 33.9 ($COCH_2$), 31.7 (—$CH_2$—), 29.4-28.8 (m, C2 & —$CH_2$—), 24.9 ($COCH_2CH_2$), 22.5 (—$CH_2$—), 14.3 (Me).

Example II-4

3-O-(6-sulfo-α-D-quinovopyranosyl)-1-O-hexanoyl-propane-1,3-diol calcium salt (10)

A sodium salt was synthesized in the same manner as Example I, except that hexanoyl chloride was used as the fatty acid derivative in the step G.

LRMS m/z 399 (M−Na)$^-$ $^1$H NMR (400 MHz, DMSO-$d_6$); δ 5.34 (br, 1H, 4'-OH), 4.56 (d, 1H, J=4.0 Hz, H1'), 4.53 (br, 1H, 3'-OH), 4.41 (d, 1H, J=6.4 Hz, 2'-OH), 4.10 (t, 2H, J=6.6 Hz, H1a & H1b), 3.83-3.77 (m, 2H, H3a & H5'), 3.41-3.33 (m, 2H, H3b & H3'), 3.21-3.16 (m, 1H, H2'), 2.98-2.92 (m, 2H, H4' & H6'a), 2.63 (dd, 1H, J=14.0, 6.0 Hz, H6'b), 2.27 (t, 2H, J=7.2 Hz, $COCH_2$), 1.82 (tt, J=6.4, 6.4 Hz, 2H, H2a & H2b), 1.52 (tt, J=7.2, 6.8 Hz, 2H, $COCH_2CH_2$), 1.30-1.26 (m, 4H, —$CH_2$—), 0.85 (t, 3H, J=6.6 Hz, Me).

$^{13}$C NMR (100 MHz, DMSO-$d_6$); δ 173.0 (C=O), 98.3 (C1'), 74.7 (C4'), 73.2 (C3'), 71.9 (C2'), 68.3 (C5'), 63.5 (C3), 61.3 (C1), 55.2 (C6'), 33.5 ($COCH_2$), 30.7 (—$CH_2$—), 28.6 (C2), 24.1 ($COCH_2CH_2$), 21.7 (—$CH_2$—), 13.7 (Me).

The sodium salt was further subjected to ion exchange treatment to obtain the title compound.

Example II-5

3-O-(6-sulfo-α-D-quinovopyranosyl)-1-O-acetyl-propane-1,3-diol calcium salt

A sodium salt was synthesized in the same manner as Example I, except that acetyl chloride was used as the fatty acid derivative in the step G.

LRMS m/z 343 (M−Na)−

$^1$H NMR (400 MHz, DMSO-$d_6$); δ 5.47-5.46 (m, 1H, 4'-OH), 4.57 (d, 1H, J=3.6 Hz, H1'), 4.50-4.49 (br, 1H, 3'-OH), 4.39-4.38 (br, 1H, 2'-OH), 4.10 (t, 2H, J=6.8 Hz, H1), 3.83-3.76 (m, 2H, H3a & H5'), 3.42-3.34 (m, 2H, H3b & H3'), 3.20-3.16 (m, 1H, H2'), 2.98 (ddd, 1H, J=9.0, 9.0, 3.2 Hz, H4'), 2.88 (dd, 1H, J=13.6, 5.6 Hz, H6'a), 2.62 (dd, 1H, J=14.0, 5.6 Hz, H6'b), 2.00 (s, 3H, Me), 1.835 (tt, 1H, J=6.4, 6.4 Hz, H2).

$^{13}$C NMR (100 MHz, DMSO-$d_6$); δ 170.4 (C=O), 98.3 (C1'), 74.6 (C4'), 73.2 (C3'), 71.9 (C2'), 68.3 (C5'), 63.5 (C3), 61.5 (C1), 55.0 (C6'), 28.5 (C2), 20.7 (Me).

The sodium salt was further subjected to ion exchange treatment to obtain the title compound.

Example II-6

3-O-(6-sulfo-α-D-quinovopyranosyl)-1-O-formyloxy-propane-1,3-diol sodium salt (10)

The title compound was obtained through the steps A-1 to F of Example I, followed by the following steps J to L.

Step J; 3-O-(2,3,4-tri-O-benzyl-6-sulfo-α-D-quinovopyranosyl)-propane-1,3-diol sodium salt (8")

To a solution of the compound (7) (542 mg, 956 μmol) in acetic acid (5.5 g), added were Oxone® (1.8 g) and potassium acetate (68 mg), and the mixture was vigorously stirred at room temperature for 48 hours. After the sufficient progress of the reaction was confirmed, the reaction liquid was poured to a chilled 7.5 M sodium hydroxide (13 ml) solution, and extracted with ethyl acetate (3×10 ml). The organic layers were combined, washed with saturated sodium hydrogen carbonate solution (2×10 ml) and saturated saline (2×10 ml), dried with sodium sulfate, filtered, and concentrated under reduced pressure. The concentrated residue was purified with silica gel chromatography (chloroform-methanol, 10:1→8:1→6:1→4:1→2:1→1:1) to obtain the title compound 8" in the form of a colorless waxy substance [401 mg (675 mmol), 70.7%].

LRMS m/z 571 (M−Na)−

$^1$H NMR (400 MHz, CD$_3$OD+CDCl$_3$); δ 7.37-7.26 (m, 15H, ArH), 4.96 (d, 1H, J=11.2 Hz, ArCH$_2$), 4.89 (d, 1H, J=11.2 Hz, ArCH$_2$), 4.80 (d, 1H, J=3.6 Hz, H1'), 4.78 (d, 1H, J=10.4 Hz, ArCH$_2$), 4.75 (d, 1H, J=11.6 Hz, ArCH$_2$), 4.66 (d, 1H, J=11.6 Hz, ArCH$_2$), 4.62 (d, 1H, J=11.2 Hz, ArCH$_2$), 4.24-4.19 (m, 1H, 5'), 4.09 (ddd, 1H, J=9.6, 8.4, 5.2 Hz, H1a), 3.97 (dd, 1H, J=9.2, 9.2 Hz, H3'), 3.80 (ddd, 1H, J=11.3, 8.0, 4.0 Hz, H3a), 3.68-3.62 (m, 1H, H3b), 3.56 (dd, 1H, J=9.6, 3.6 Hz, H2'), 3.46 (ddd, 1H, J=9.8, 5.4, 5.4 Hz, H1b), 3.32-3.23 (m, 2H, H6'a & H4'), 2.93 (dd, 1H, J=14.0, 9.8 Hz, H6'b), 1.98-1.81 (m, 2H, H2a & H2b).

$^{13}$C NMR (100 MHz, CD$_3$OD+CDCl$_3$); δ 139.0 (Ar-ipso), 138.5 (Ar-ipso), 138.4 (Ar-ipso), 128.9-128.1 (m, Ar), 96.8 (C1'), 82.4 (C3'), 81.0 (C4'), 80.6 (C2'), 76.1 (ArCH$_2$), 75.5 (ArCH$_2$), 73.6 (ArCH$_2$), 67.9 (C5'), 65.5 (C1), 59.6 (C3), 52.8 (C6'), 32.6 (C2).

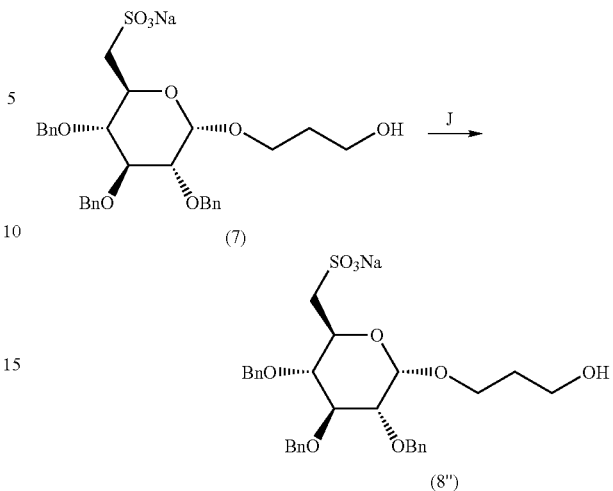

Step K; 3-O-(6-sulfo-α-D-quinovopyranosyl)-propane-1,3-diol sodium salt (9")

To a solution of the compound (8") (534 mg, 898 μmol) in methanol (20 ml) and chloroform (5.0 ml), added was 10% palladium activated carbon (135 mg), and the mixture was stirred at room temperature for 16 hours in a hydrogen gas atmosphere. After the sufficient progress of the reaction was confirmed, palladium activated carbon was collected by filtration, and the filtrate was concentrated under reduced pressure. To the obtained residue, added were methanol (20 ml) and toluene (20 ml), the mixture was vigorously stirred, and the solvent was removed by evaporation under reduced pressure to obtain a mixture in the form of a colorless liquid (320 mg). The presence of the title compound in the mixture was confirmed by LRMS. The mixture containing the title compound (9") was then subjected to the subsequent reaction.

LRMS m/z 301 (M−Na)

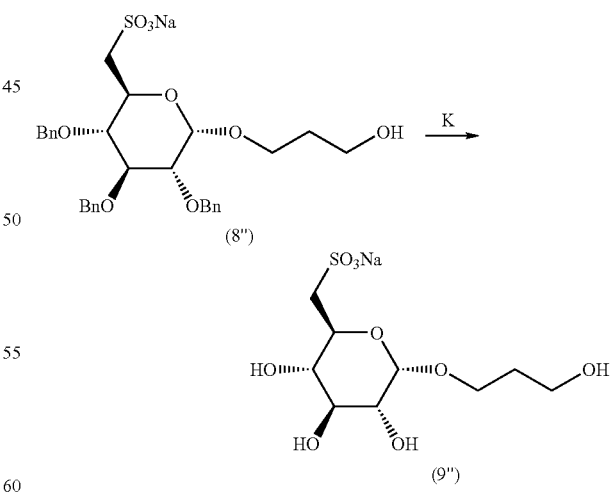

Step L; 3-O-(6-sulfo-α-D-quinovopyranosyl)-1-O-formyloxy-propane-1,3-diol sodium salt (10)

A mixture containing the compound (9") (70 mg), 1-ethyl-3-(3-dimethylaminopropyl)carbodiimide hydrochloride (EDCI.HCl) (93 mg, 487 μmol), and 4-dimethylaminopyridine (12 mg, 97 μmol) were dissolved in anhydrous N,N-dimethylformamide (DMF, 10 ml), formic acid (14 mg, 259 μmol) was added dropwise to the solution under cooling with ice, and allowed to react at room temperature for 18 hours. After the sufficient progress of the reaction was confirmed, water (1.0 ml) was poured to the reaction liquid to stop the reaction, and then the solution was concentrated under reduced pressure. The obtained residue was purified with silica gel chromatography (chloroform-methanol-water, 3:1:0.1→2:1:0.1→1:1:0.1) to obtain the title compound 10 in the form of a colorless oily substance [12 mg (33 μmol), 16.7%].

LRMS m/z 329 (M−Na)⁻

$^{1}$H NMR (400 MHz, DMSO-$d_6$); δ 8.18 (s, 1H, O=CH), 4.56 (d, 1H, J=3.6 Hz, H1'), 4.20 (t, 2H, J=6.8 Hz, H1a & H1b), 3.86-3.78 (m, 2H, H3a & H5'), 3.41-3.31 (m, 2H, H3b & H3'), 3.18 (dd, 1H, J=9.6, 4.0 Hz, H2'), 3.03-2.90 (m, 2H, H4' & H6'a), 2.63-2.58 (m, 1H, H6'b), 1.86 (tt, J=6.4, 6.4 Hz, 2H, H2a & H2b)

$^{13}$C NMR (100 MHz, DMSO-$d_6$); δ 162.2 (C=O), 98.4 (C1'), 74.7 (C4'), 73.2 (C3'), 71.9 (C2'), 68.4 (C5'), 63.3 (C3), 61.2 (C1), 55.1 (C6'), 26.1 (C2).

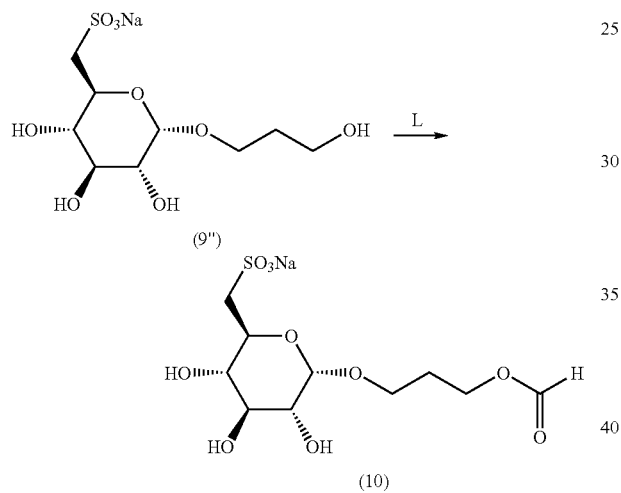

Example III

Another example of the process for preparing the β-sulfoquinovosylacyl propanediol compound according to the present invention is described below.

Example III-1

3-O-(6-sulfo-β-D-quinovopyranosyl)-1-O-oleoyl-propane-1,3-diol sodium salt

The title compound was synthesized through the procedure according to the following scheme.

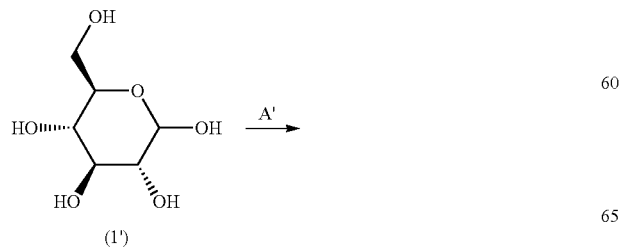

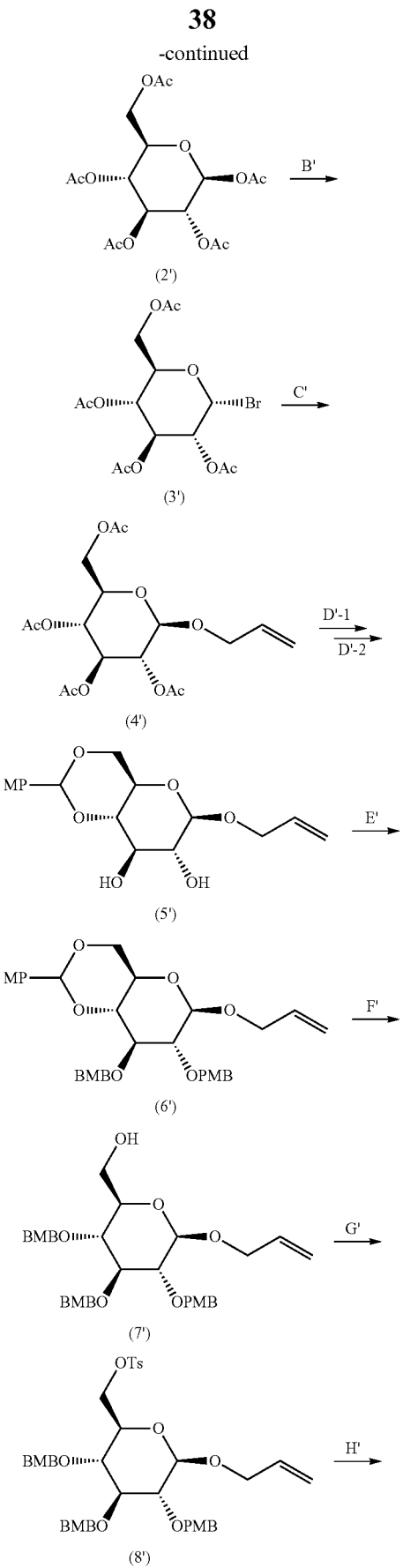

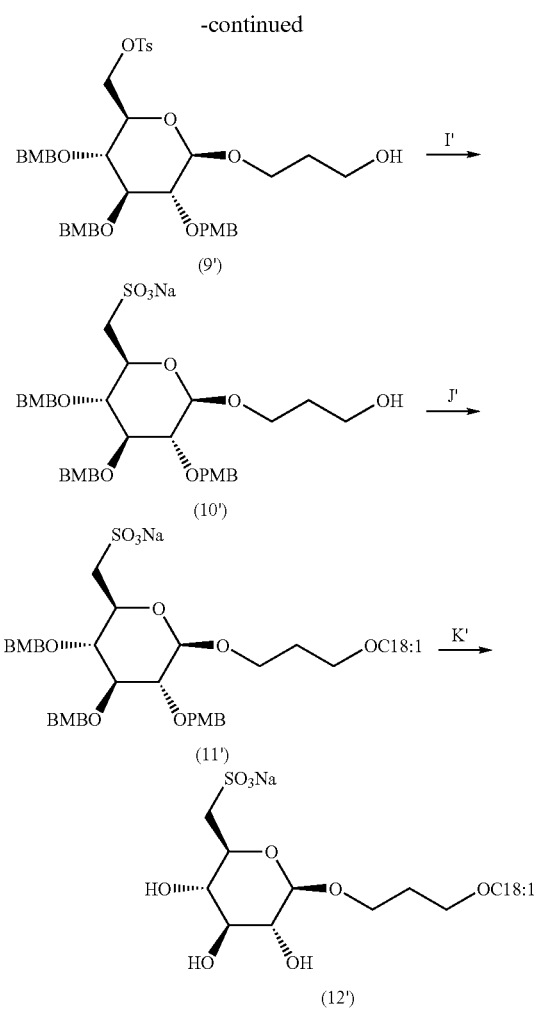

A') acetic anhydride, sodium acetate, heating and boiling, 55.3%;

B') hydrobromic acid-acetic acid solution, dichloromethane, room temperature, 6 hours, 58.5%;

C') allyl alcohol, cyanide mercury, dichloromethane, room temperature, 16 hours, 64.4%;

D') D'-1. sodium methoxide, methanol, room temperature, 4 hours;

D'-2. p-anisaldehyde dimethyl acetal, p-toluenesulfonic acid monohydrate, acetonitrile, 40° C., 16 hours, 95.3%;

E') p-methoxybenzyl chloride, sodium hydroxide, N,N-dimethylformamide, room temperature, 16 hours, 92.0%;

F') aluminum lithium hydride, aluminum chloride, dichloromethane, diethyl ether, 0° C., 1 hour, 73.3%;

G') p-toluenesulfonyl chloride, 4-dimethylaminopyridine, pyridine, room temperature, 16 hours, 85.9%;

H') 9-borabicyclononane, tetrahydrofuran, room temperature, 16 hours; water, sodium hydroxide, hydrogen peroxide water, room temperature, 4 hours, 93.5%;

I') sodium sulfite, ethanol, water, heating under reflux, 72 hours, 90.2%;

J') oleic acid anhydride, 4-dimethylaminopyridine, pyridine, dichloromethane, heating under reflux, 16 hours, 67.6%; and K') 2,3-dichloro-5,6-dicyano-1,4-benzoquinone, dichloromethane, methanol, water, room temperature, 4 hours, 55.9%.

$[\alpha]^{21}_D$ −3.1° (c1.00 CH$_3$OH), LRMS m/z 565 (M−Na)$^-$, HRMS calcd for C$_{27}$H$_{49}$O$_{10}$S (M−Na)$^-$ 565.3051. found 565.3059.

$^1$H NMR (400 MHz, CD$_3$OD); δ 5.37-5.30 (m, 2H, —CH═CH—), 4.27 (d, 1H, J=7.84 Hz, H1'), 4.23-4.13 (m, 2H, H1a & H1b), 4.01-3.96 (m, 1H, H3a), 3.72 (ddd, 1H, J=9.64, 8.62, 2.20 Hz, H5'), 3.68-3.62 (m, 1H, H3b), 3.38 (dd, 1H, J=14.4, 2.20 Hz, H6'a), 3.36 (t, 1H, J=9.08 Hz, H3'), 3.19 (dd, 1H, J=9.20, 7.88 Hz, H2'), 3.13 (t, 1H, J=9.28 Hz, H4'), 2.98 (dd, 1H, J=14.4, 8.62 Hz, H6'b), 2.31 (t, 2H, J=7.46 Hz, COCH$_2$), 2.04-2.00 (m, 4H, —CH$_2$CH═CHCH$_2$—), 1.97-1.90 (m, 2H, H2a & H2b), 1.62-1.56 (m, 2H, COCH$_2$CH$_2$), 1.31-1.29 (br, 20H, —CH$_2$—), 0.89 (t, 3H, J=6.84 Hz, Me).

$^{13}$C NMR (100 MHz, CD$_3$OD); δ 175.7 (C═O), 130.9 (—CH═CH—), 130.8 (—CH═CH—), 104.2 (C1'), 77.9 (C3'), 75.1 (C2'), 74.7 (C4'), 73.7 (C5'), 67.3 (C3), 62.8 (C1), 54.3 (C6'), 35.1 (COCH$_2$), 33.1 (—CH$_2$—), 30.8-30.1 (m, C2 & —CH$_2$—), 28.1 (—CH$_2$CH═CHCH$_2$—), 26.1 (COCH$_2$CH$_2$), 23.8 (—CH$_2$—), 14.5 (Me).

Example III-2

3-O-(6-sulfo-β-D-quinovopyranosyl)-1-O-stearoyl-propane-1,3-diol sodium salt

The title compound was synthesized in the same manner as Example III-1, except that stearoyl chloride was used in place of oleic acid anhydride.

$[\alpha]^{22}_D$ −4.7° (c1.00H$_2$O), LRMS m/z 567 (M−Na)$^-$, HRMS calcd for C$_{27}$H$_{51}$O$_{10}$S (M−Na)$^-$ 567.3208. found 567.3211.

$^1$H NMR (400 MHz, DMSO-d$_6$); δ 5.56 (d, 1H, J=3.16 Hz, 4'-OH), 4.81 (d, 1H, J=4.92 Hz, 2'-OH), 4.74 (d, 1H, J=4.64 Hz, 3'-OH), 4.09 (d, 1H, J=7.76 Hz, H1'), 4.07 (t, 2H, J=6.60 Hz, H1a & H1b), 3.77 (dt, 1H, J=10.2, 6.27 Hz, H3a), 3.54-3.45 (m, 2H, H3b & H5'), 3.13 (dt, 1H, J=8.80, 4.68 Hz, H3'), 2.99 (dt, 1H, J=9.14, 3.08 Hz, H4'), 2.97-2.91 (m, 2H, H2' & H6'a), 2.68 (dd, 1H, J=13.9, 5.24 Hz, H6'b), 2.27 (t, 2H, J=7.40 Hz, COCH$_2$), 1.86-1.78 (m, 2H, H2a & H2b), 1.54-1.47 (m, 2H, COCH$_2$CH$_2$), 1.24 (br, 28H, —CH$_2$—), 0.86 (t, 3H, J=6.88 Hz, Me).

$^{13}$C NMR (100 MHz, DMSO-d$_6$); δ 172.9 (C═O), 102.8 (C1'), 76.1 (C3'), 74.6 (C4'), 73.4 (C2'), 72.5 (C5'), 65.2 (C3), 61.2 (C1), 55.6 (C6'), 33.6 (COCH$_2$), 31.3 (C2), 29.0-28.5 (m, —CH$_2$—), 24.5 (COCH$_2$CH$_2$), 22.1 (—CH$_2$—), 13.9 (Me).

Analysis

Example IV

Example IV-1

Analysis with High Performance Liquid Chromatography and Mass Spectrometry

The 3-O-(6-sulfo-α-D-quinovopyranosyl)-1-O-stearoyl-propane-1,3-diol sodium salt and 3-O-(6-sulfo-α-D-quinovopyranosyl)-1-O-stearoyl-glycerol sodium salt were separated and detected by high performance liquid chromatography and electrospray mass spectrometry.

The test substance was dissolved in 5% acetonitrile in 5 mmol/l ammonium acetate aqueous solution, diluted with the solvent to an intended concentration, and then analyzed by high performance liquid chromatography equipped with CapCellPak® C18MG (column size; 2.0×50 mm, manufactured by Shiseido Co., Ltd.). The separation conditions were as follows: the column temperature was 40° C., the flow rate was 0.2 ml per minute, and elution was conducted over a period of 20 minutes with a linear concentration gradient of 50% to 70% of acetonitrile with reference to the above-described solvent.

The eluted test substance was detected with a Bruker Esquire 3000 plus ion mass spectrometer, and the detection ion mode was total ion chromatography (TIC), and the detection mass range was m/z=100 to 1000.

Figure 2:
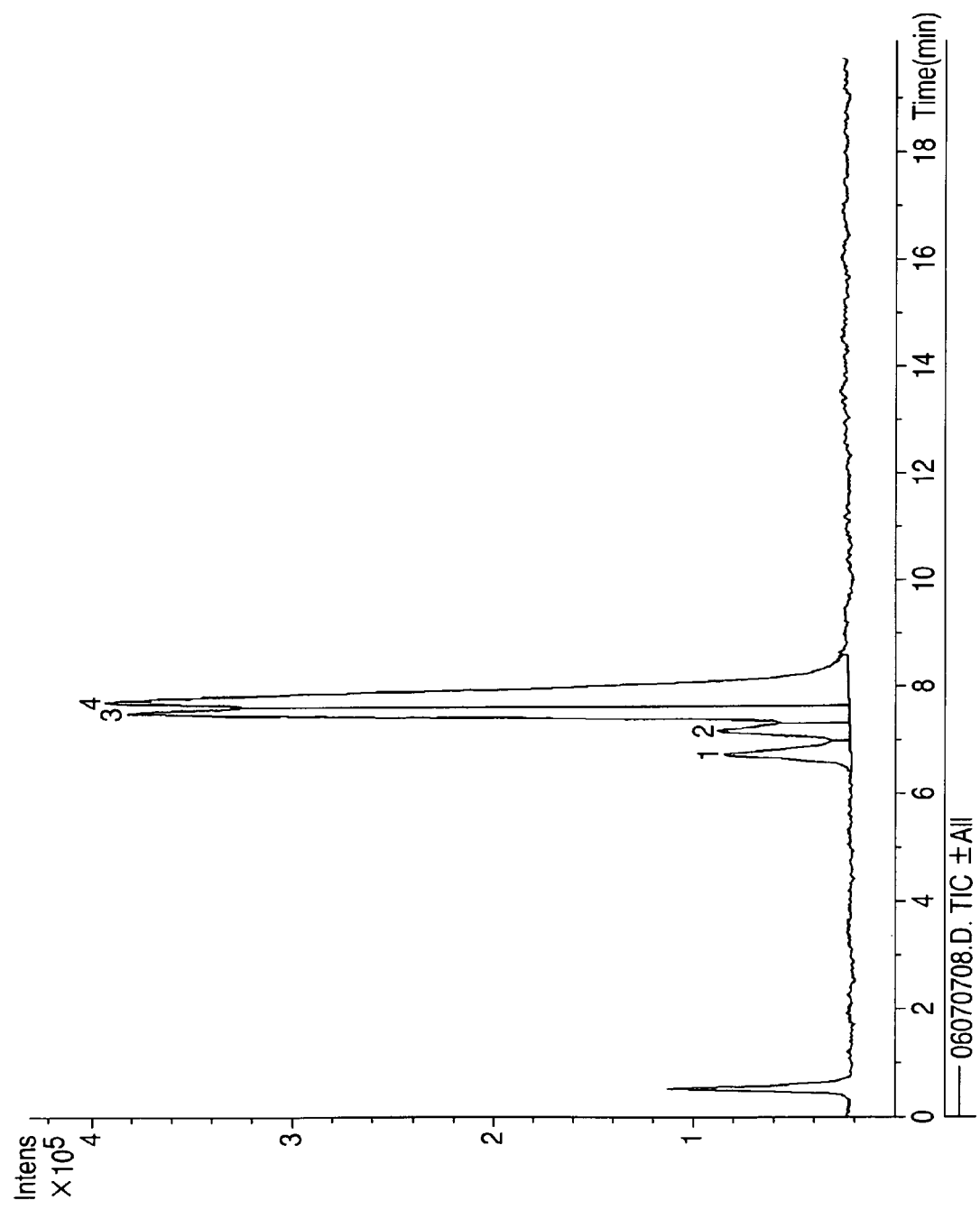
FIG. 2 is a chromatogram showing the result of analysis of αSQMG C18:0.

FIGS. 1 and 2 show the chromatograms of the test substance.

The analysis result indicates that, as shown in FIG. 1, the 3-O-(6-sulfo-α-D-quinovopyranosyl)-1-O-stearoyl-propane-1,3-diol sodium salt exhibited a single peak, while the 3-O-(6-sulfo-α-D-quinovopyranosyl)-1-O-stearoyl-glycerol sodium salt shown in FIG. 2 exhibited minor peaks representing a structural isomer at 6.8 minutes (peak No. 1) and 7.3 minutes (peak No. 2), which suggests acyl transfer from the 1-position to 2-position in the glycerol moiety, and major peaks representing a diastereo isomer (diastereomer) αSQMG C18:0 at 7.6 minutes (peak No. 3) and 7.8 minutes (peak No. 4).

These results indicate that the 3-O-(6-sulfo-α-D-quinovopyranosyl)-1-O-stearoyl-propane-1,3-diol sodium salt according to an aspect of the present invention has a very high purity in comparison with a known compound, 3-O-(6-sulfo-α-D-quinovopyranosyl)-1-O-stearoyl-glycerol sodium salt.

Example IV-2

Solubility Measurement 1 g each of the sodium salt and calcium salt of 3-O-(6-sulfo-α-D-quinovopyranosyl)-1-O-stearoyl-propane-1,3-diol was placed in 5 ml of injectable water (manufactured by Otsuka Pharmaceutical Co., Ltd.), strongly shaken at 25° C.; they were immediately dissolved. This fact suggests that the substance is evaluated as "readily soluble" by the criteria described in the general rules Japanese Pharmacopeia.

These results indicate that αSQAP has very high solubility. In addition, although not shown herein, SQAP series according to the present invention other than the salts of 3-O-(6-sulfo-α-D-quinovopyranosyl)-1-O-stearoyl-propane-1,3-diol also have high solubility. Such high solubility facilitates dissolution of a necessary amount of the substance in a small amount of a solvent. As a result of this, for example, an injection to be administered to a subject can be readily prepared. In addition, such high water solubility is advantageous in preparation of injections, as well as other various formulations such as oral agents.

Pharmacological Tests.

The pharmacological activity of the sulfoquinovosylacyl propanediol compound according to the present invention was examined.

Example V

Radiosensitizing Effect Test

The radiosensitizing effect was examined through tumor-bearing mouse experiment.

Example V-1

Human Esophageal Squamous Cell Carcinoma (No. 1)

Figure 3:
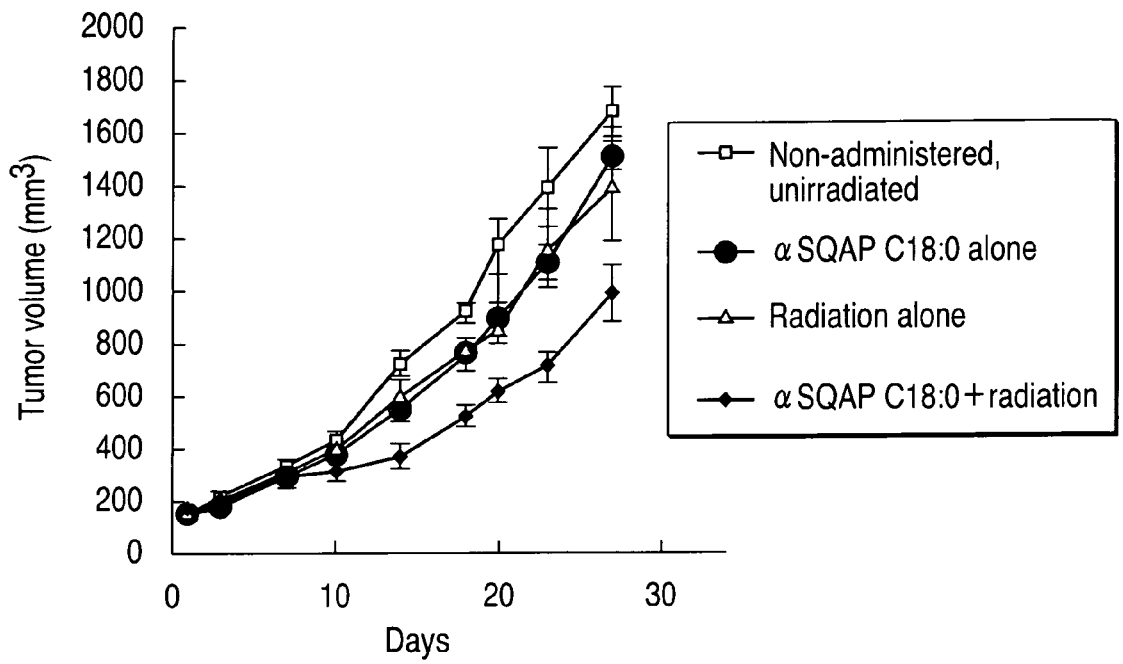
FIG. 3 is a graph showing the effect of a test substance on the increase of tumor volume.

Human esophageal squamous cell carcinoma cells TE-8 were transplanted into the right femoral region of KSN nude mice in a ratio of $1 \times 10^6$ cells per individual. Subsequently, the mice were bred for about 14 days to form a tumor mass of about 150 mm$^3$ in each individual. Thereafter, four mice were assigned to each of the following groups (1) to (4):

(1) non-administered, un-irradiated group (in FIG. 3, indicated with white squares);

(2) non-administered, radiotherapy-treated group (in FIG. 3, indicated with white triangles);

(3) αSQAP C18:0-administered, un-irradiated group (in FIG. 3, indicated with black circles); and (4) αSQAP C18:0-administered, radiotherapy-treated group (in FIG. 3, indicated with black rhombuses).

The drug was administered from Day 1 to Day 5, 2 mg/kg once a day. The subjects were exposed to radiation emitted from an X-ray generator (HS-225, manufactured by Shimadzu Co., Ltd.) at a dose of 2 Gy on Day 1 and Day 4. The tumor volume was calculated according to the calculation formula: (minor axis)$^2$×major axis×0.5. The results are shown in FIG. 3.

In all the groups, the tumor volume steadily increased from the start to end of the test. However, from about Day 10, the increment of the tumor volume in the groups (2) to (4) fell below that in the (1) non-administered, un-irradiated group. In addition, suppression of the increase of the tumor volume in the (2) non-administered, radiotherapy-treated group and (3) αSQAP C18:0-administered, un-irradiated group was at the same level. The increase of the tumor volume was most suppressed in the (4) αSQMG C18:0-administered, radiotherapy-treated group in comparison with other groups.

Example V-2

Human Esophageal Squamous Cell Carcinoma (No. 2)

This experiment was conducted in the same manner as Example V-1, except that the drug dose administered from Day 1 to Day 5 was 1 mg/kg once a day, and the radiation dose was 4 Gy, and the tumor volume was measured. The results are shown in FIG. 4.

Figure 4:
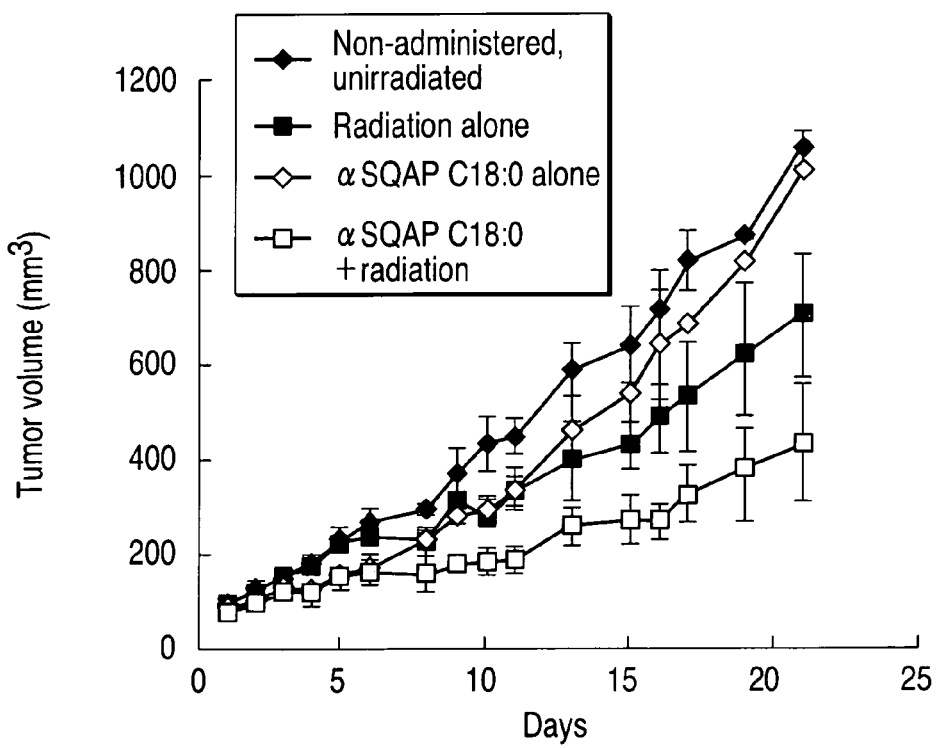
FIG. 4 is a graph showing the effect of a test substance on the increase of tumor volume.

Details about the groups are as follows:

(1) non-administered, un-irradiated group (in FIG. 4, indicated with black rhombuses);

(2) non-administered, radiotherapy-treated group (in FIG. 4, indicated with black squares);

(3) αSQAP C18:0-administered, un-irradiated group (in FIG. 4, indicated with white rhombuses); and (4) αSQAP C18:0-administered, radiotherapy-treated group (in FIG. 4, indicated with white squares).

The results indicate that, in all the groups, the tumor volume increased with the lapse of time. The increment in the tumor volume in the groups (2) to (4) was smaller than that in the (1) non-administered, un-irradiated group. In addition, the increase of the tumor volume was most strongly suppressed in the (4) αSQAP C18:0-administered, radiotherapy-treated group in comparison with other groups.

Example V-3

Human Colonic Adenocarcinoma

Human colonic adenocarcinoma cells SW480 were transplanted into the right femoral region of KSN nude mice in a ratio of $1 \times 10^6$ cells per individual. Subsequently, the mice were bred for about 14 days to form a tumor mass of about 150 mm$^3$ in each individual.

Figure 5:
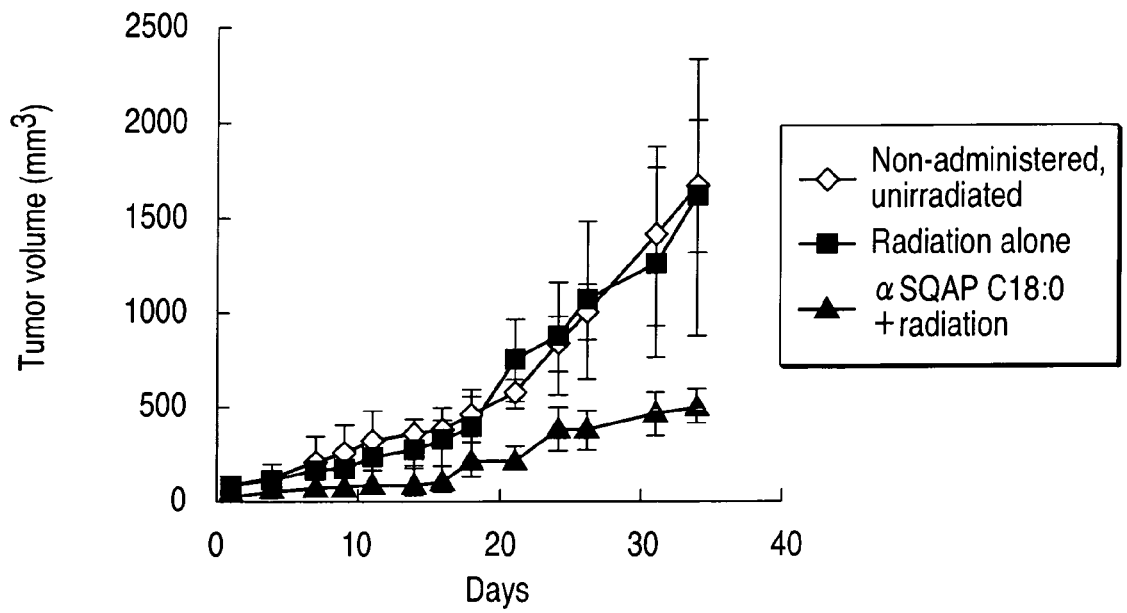
FIG. 5 is a graph showing the effect of a test substance on the increase of tumor volume.

Thereafter, four mice were assigned to each of the three groups (1) to (3):

(1) non-administered, un-irradiated group (in FIG. 5, indicated with white rhombuses);

(2) non-administered, radiotherapy-treated group (in FIG. 5, indicated with black squares); and (3) αSQAP C18:0-administered, radiotherapy-treated group (in FIG. 5, indicated with black triangles).

The drug was administered from Day 1 to Day 5, 2 mg/kg once a day. The subjects were exposed to radiation emitted from an X-ray generator (HS-225, manufactured by Shimadzu Co., Ltd.) at a dose of 2 Gy on Day 1 and Day 4. The tumor volume was calculated according to the calculation formula: (minor axis)$^2$×major axis×0.5. The results are shown in FIG. 5.

The results indicate that, in all the groups, the tumor volume increased with the lapse of time. However, the increase of the tumor volume in the (1) non-administered, un-irradiated group and (2) non-administered, radiotherapy-treated group was alike, but the increase of the tumor volume in the (3) αSQAP C18:0-administered, radiotherapy-treated group was suppressed from the initial stage of the experiment, and the increase of the tumor volume was markedly suppressed in general.

The following Examples V-4, 5, 6, and Examples VI to VIII used an SQAP compound which had been calcium(salt)-substituted through ion exchange treatment.

Example V-4

Human Colonic Adenocarcinoma

Figure 6:
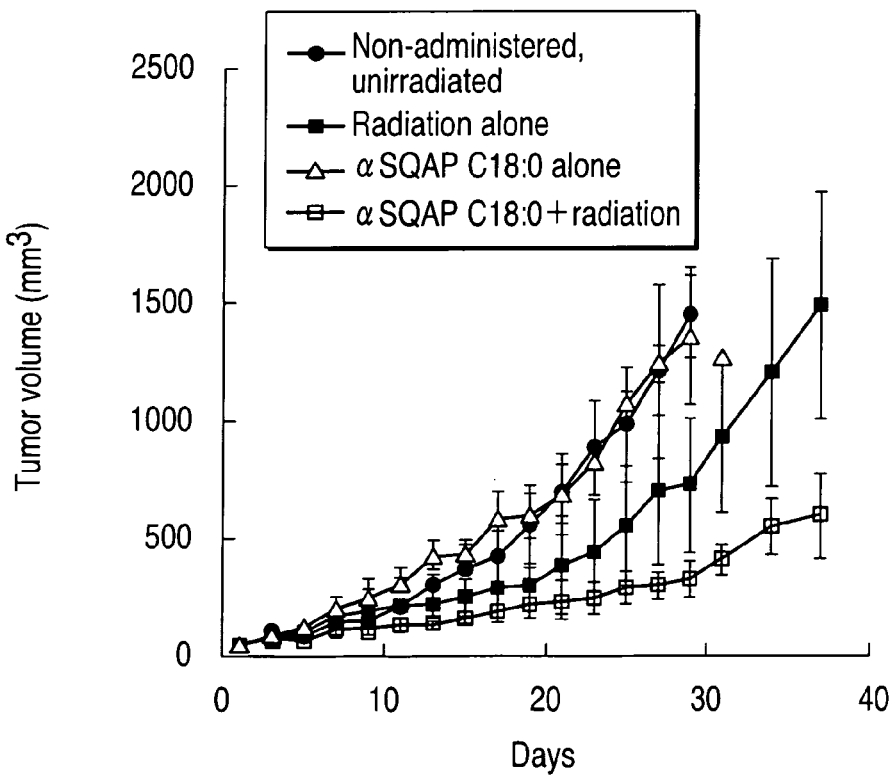
FIG. 6 is a graph showing the effect of a test substance on the increase of tumor volume.

Human colonic adenocarcinoma cells SW480 were transplanted into the right femoral region of KSN nude mice in a ratio of 2×10$^6$ cells per individual. After a tumor mass of about 50 mm$^3$ was formed in each individual, four mice were assigned to each of the four groups (1) to (4):

(1) non-administered, un-irradiated group (in FIG. 6, indicated with black circles);

(2) non-administered, radiotherapy-treated group (in FIG. 6, indicated with black squares);

(3) αSQAP C18:0-administered, un-irradiated group (in FIG. 6, indicated with white triangles); and (4) αSQAP C18:0-administered, radiotherapy-treated group (in FIG. 6, indicated with white squares).

The drug was administered from the tail vein from Day 1 to Day 5, 1 mg/kg once a day. The subjects were exposed to radiation emitted from an X-ray generator (HS-225, manufactured by Shimadzu Co., Ltd.) at a dose of 2 Gy on Day 1 and Day 4.

The results are shown in FIG. 6, indicating that the tumor volume increased with time in all the groups. However, the increase of the tumor volume was most suppressed in the (4) αSQAP C18:0-administered, radiotherapy-treated group in comparison with other groups.

Example V-5

Human Esophageal Squamous Cell Carcinoma

Human esophageal squamous cell carcinoma cells TE-8 were transplanted into the right femoral region of KSN nude mice in a ratio of 1×10$^6$ cells per individual. After a tumor mass of about 50 mm$^3$ was formed in each individual, four mice were assigned to each of the four groups (1) to (4):

(1) non-administered, un-irradiated group (in FIG. 7, indicated with black rhombuses);

(2) non-administered, radiotherapy-treated group (in FIG. 7, indicated with black circles);

(3) αSQAP C10:0-administered, un-irradiated group (in FIG. 7, indicated with white triangles); and (4) αSQAP C10:0-administered, radiotherapy-treated group (in FIG. 7, indicated with white squares).

The drug was administered intraperitoneally from Day 1 to Day 5, 1 mg/kg once a day. The subjects were exposed to radiation emitted from an X-ray generator (HS-225, manufactured by Shimadzu Co., Ltd.) at a dose of 4 Gy on Day 1 and Day 4.

The results are shown in FIG. 7, indicating that the tumor volume increased with time in all the groups. However, the increase of the tumor volume was most suppressed in the (4) αSQAP C10:0-administered, radiotherapy-treated group in comparison with other groups.

Example V-6

Human Esophageal Squamous Cell Carcinoma

Human esophageal squamous cell carcinoma cells TE-8 were transplanted into the right femoral region of KSN nude mice in a ratio of 1×10$^6$ cells per individual. After a tumor mass of about 50 mm$^3$ was formed in each individual, four mice were assigned to each of the four groups (1) to (4):

(1) non-administered, un-irradiated group (in FIG. 8, indicated with black rhombuses);

(2) non-administered, radiotherapy-treated group (in FIG. 8, indicated with black squares);

(3) αSQAP C18:0-administered, un-irradiated group (in FIG. 8, indicated with white squares); and (4) αSQAP C18:0-administered, radiotherapy-treated group (in FIG. 8, indicated with white circles).

The drug was administered intraperitoneally from Day 1 to Day 5, 1 mg/kg once a day. The subjects were exposed to radiation emitted from an X-ray generator (HS-225, manufactured by Shimadzu Co., Ltd.) at a dose of 4 Gy on Day 1 and Day 4.

The results are shown in FIG. 8, indicating that the tumor volume increased with time in all the groups. However, the increase of the tumor volume was most suppressed in the (4) αSQAP C18:0-administered, radiotherapy-treated group in comparison with other groups.

Example VI

Antineoplastic Effect Test

Figure 9:
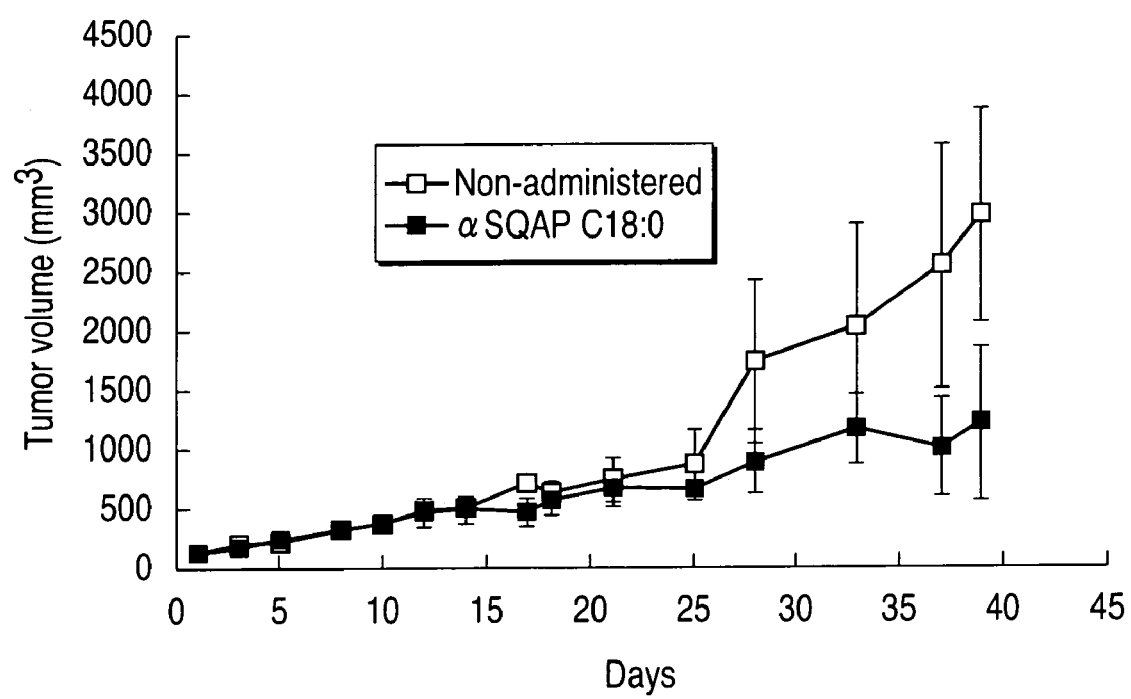
FIG. 9 is a graph showing the effect of a test substance on the increase of tumor volume.

Human colonic adenocarcinoma cells SW480 were transplanted into the right femoral region of KSN nude mice in a ratio of 2×10$^6$ cells per individual. After a tumor mass of about 50 mm$^3$ was formed in each individual, four mice were assigned to each of the two groups (1) and (2):

(1) non-administered (in FIG. 9, indicated with white squares); and (2) αSQAP C18:0-administered (in FIG. 9, indicated with black squares).

The drug was administered intraperitoneally from Day 1 to Day 14, 20 mg/kg once a day.

The results are shown in FIG. 9, indicating that the increase of the tumor volume was markedly suppressed in the αSQAP C18:0-administered group in comparison with the non-administered group.

Example VII

Tube Formation Inhibition Test Using Vascular Endothelial Cell-Fibrocyte Cocultivation System Using a angiogenesis kit (KZ-1000) manufactured by Kurabo Industries Ltd., which is a cocultivation system for human vascular endothelial cells and human fibrocytes, the effects of αSQAP C10:0, αSQAP C14:0, αSQAP C18:0, αSQAP C22:0, βSQAP C18:0, and βSQAP C18:1 on tube formation were examined. Cultivation for tube formation using the kit was conducted according to the manufacturer's instruction manual.

Using a medium containing a final concentration of 10 ng/ml of VEGF-A and being designed specifically for angiogenesis, the respective SQAP compounds were prepared to have intended concentrations. On Day 1 of the cell cultivation, special media each containing SQAP compounds at the respective concentrations and DMSO (negative control) were added to the cultivation systems. The systems were cultivated for 30 minutes, and irradiated with 2 Gy of cobalt 60. Thereafter, on Days 4, 7, and 10 of the cultivation, the media were replaced with newly prepared special media containing SQAP or DMSO. The media were removed on Day 11 of the cultivation, fixed with 70% ethanol, and the formed tubes were stained with anti-human CD31 antibody. The stained figures were photographed under an optical microscope, and the quantity of tube formation was calculated by the image analysis. The angiogenesis index was calculated according to the manufacturer's instruction manual.

Figure 10:
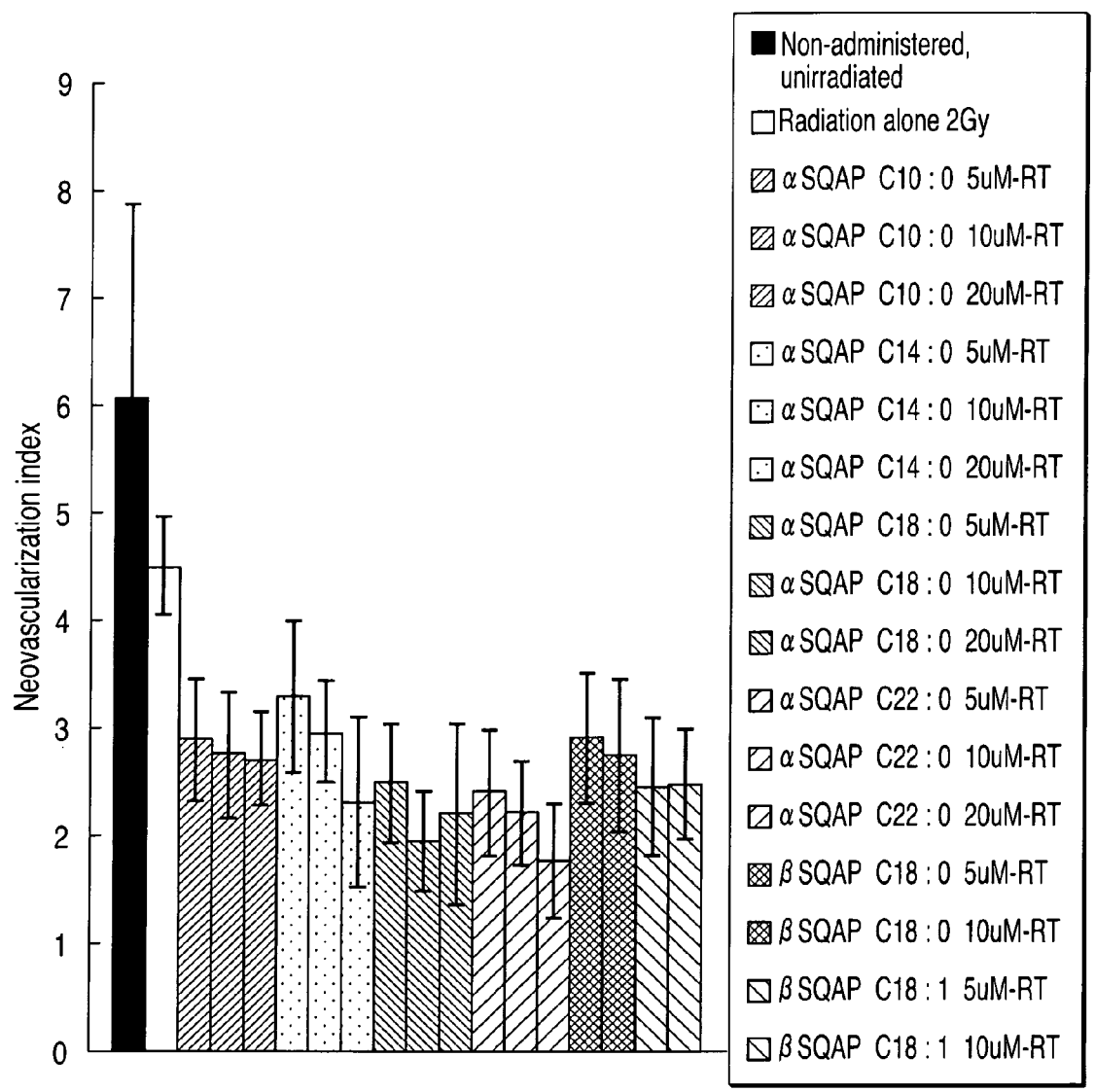
FIG. 10 is a graph showing the effect of a test substance on the tube formation.

The results are shown in FIG. 10. In comparison with the control group not treated with the SQAP compound and/or radiation therapy, the groups subjected to radiation alone (2 Gy) and/or the SQAP compounds exhibited lower angiogenesis indexes. In FIG. 10, "RT" is an abbreviation of radiation therapy. Further, those treated with the SQAP compounds exhibited lower indexes than the group treated with 2 Gy radiation alone. When combined with 2 Gy radiation, αSQAP C10:0 at final concentrations of 5, 10, and 20 μM, αSQAP C14:0 at final concentrations of 5, 10, and 20 μM, αSQAP C18:0 at final concentrations of 5, 10, and 20 μM, αSQAP C22:0 at final concentrations of 5, 10, and 20 μM, and βSQAP C18:0 at final concentrations of 5 and 10 μM, and βSQAP C18:1 at final concentrations of 5 and 10 μM inhibited tube formation in a concentration-dependent manner.

Example VIII

Toxicity Tests

Example VIII-1

Ames test

A reverse mutation assay (Ames test) was conducted using αSQAP C18:0.

Five strains composed of two strains of *Salmonella typhimurium*, which are base pair substitution mutants, and one strain of *Escherichia coli*, and two strains of *Salmonella typhimurium*, which are frameshift mutants were used as indicator bacterial strains. These strains were precultivated in the presence of αSQAP C18:0, and transferred to agar plates and cultivated thereon for 48 hours, and then the number of revertant colonies on the plate was counted. The amounts of αSQAP C18:0 added to the respective plates were 2 μg, 7 μg, 21 μg, 62 μg, 185 μg, 556 μg, 1667 μg, and 5000 μg. Regardless of the presence or absence of S9 mix added during the precultivation (wherein S9 mix is a solution prepared by adding cofactor-1 to a supernatant fraction of a liver homogenate prepared from the liver of a male rat pretreated with phenobarbital and 5,6-benzoflavone), for all the strains, the number of revertant colonies did not increase. From this fact, mutagenicity of the substance was evaluated as negative.

Example VIII-2

Micronucleus Test

Micronucleus test was conducted by rat intravenous administration using the αSQAP C18:0 calcium salt.

Five male SD rats were assigned to each of the six groups (1) to (6):
(1) non-administered group;
(2) 25 mg/kg αSQAP C18:0-administered group;
(3) 50 mg/kg αSQAP C18:0-administered group;
(4) 100 mg/kg αSQAP C18:0-administered group;
(5) 200 mg/kg αSQAP C18:0-administered group; and
(6) positive control group (2 mg/kg mitomycin C-administered group).

The test solutions for (1) to (5) contained a normal saline solution containing 10% CREMOPHOR EL as the solvents, and the above-described doses were administered to the rats twice in total for two consecutive days. To the positive control group, the above-described dose was administered once.

About 24 hours after the administration, bone marrow smears were prepared. Two thousands of immature erythrocytes were counted for each individual, and the incidence of immature erythrocytes having a micronucleus was calculated. As the index of marrow proliferation suppression, the proportion of immature erythrocytes contained in 1000 erythrocytes was calculated. The result indicates that no significant increase was found in the incidence of micronuclei in the test substance-administered group in comparison with the non-administered group. In addition, no influence was found on the marrow proliferation suppression in the test substance-administered group. From these facts, the substance was evaluated as inducing no chromosomal aberration in bone marrow cells.

Example VIII-3

Single Dose Toxicity Test

Using αSQAP C18:0, an acute toxicity test was conducted on rats. Five female and five male SD rats of 5 to 6 weeks old were assigned to each of the groups (1) to (7):
(1) non-administered group;
(2) 25 mg/kg αSQAP C18:0-administered group;
(3) 50 mg/kg αSQAP C18:0-administered group;
(4) 100 mg/kg αSQAP C18:0-administered group;
(5) 200 mg/kg αSQAP C18:0-administered group;
(6) 400 mg/kg αSQAP C18:0-administered group; and
(7) 800 mg/kg αSQAP C18:0-administered group.

The test solution for (1) and (4) to (7) contained a normal saline solution containing 10% CREMOPHOR EL, (2) contained a normal saline solution containing 2.5% CREMOPHOR EL, and (3) contained a normal saline solution containing 5% CREMOPHOR EL as the solvents.

These test solutions were administered via the rat tail vein at a rate of 0.13 ml/kg/minute, and the clinical signs were observed for two days including the date of administration. No individual died during the test period, and the lethal dose was estimated to be higher than 800 mg/kg.

Other benefits and modifications would be readily understood by those skilled in the art. Accordingly, it is evident that the present invention in its broader aspect is not limited to the specific details and representative embodiments shown and described herein. Accordingly, various modifications may be made without departing from the spirit or scope of the general inventive concept as defined by the appended claims and their equivalents.

The compound of the present invention is a novel substance, and, as described above, has remarkable radiosensitizing effect and antineoplastic effect. The compound of the present invention is obtainable at high purity by a simple synthesis method. Further, the compound of the present invention is structurally stable, and highly soluble in water. Accordingly, the compound is advantageous in its manufacture and formulation when used as a drug, and is also advantageous in the use after storage as a compound and a drug. In addition, the compound features low toxicity. Accordingly, the compound is very advantageous as a drug to be administered to human and other animals over a short or long period.

The present invention is funded by Special Coordination Funds for Promoting Science and Technology provided by the Ministry of Education, Culture, Sports, Science and Technology.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

What is claimed is:

1. A sulfoquinovosylacyl propanediol compound represented by formula (I):

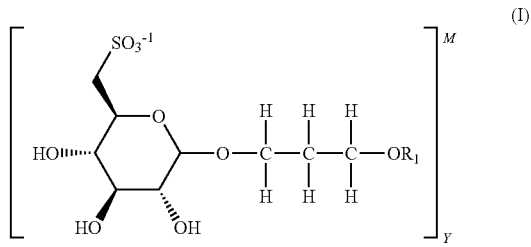

wherein $R_1$ is an acyl residue of a fatty acid, and M represents a hydrogen ion or a metal ion, and wherein the acyl residue has 26 or less and 1 or more carbon atoms,
or a pharmaceutically acceptable salt thereof.

2. The sulfoquinovosylacyl propanediol compound according to claim 1, wherein the acyl residue has 22 or less and 1 or more carbon atoms.

3. The sulfoquinovosylacyl propanediol compound according to claim 1, wherein M is a hydrogen atom.

4. The sulfoquinovosylacyl propanediol compound according to claim 1, wherein M is selected from the group consisting of sodium, potassium, calcium and magnesium.

5. The sulfoquinovosylacyl propanediol compound according to claim 1, wherein the metal ion has a charge of +1, +2 or +3.

6. The sulfoquinovosylacyl propanediol compound according to claim 1, wherein the compound is selected from the group consisting of
3-O-(6-sulfo-α-D-quinovopyranosyl)-1-O-stearoyl-propane-1,3-diol sodium salt;
3-O-(6-sulfo-α-D-quinovopyranosyl)-1-O-stearoyl-propane-1,3-diol calcium salt;
3-O-(6-sulfo-α-D-quinovopyranosyl)-1-O-decanoyl-propane-1,3-diol sodium salt;
3-O-(6-sulfo-α-D-quinovopyranosyl)-1-O-decanoyl-propane-1,3-diol calcium salt;
3-O-(6-sulfo-α-D-quinovopyranosyl)-1-O-myristoyl-propane-1,3-diol sodium salt;
3-O-(6-sulfo-α-D-quinovopyranosyl)-1-O-myristoyl-propane-1,3-diol calcium salt;
3-O-(6-sulfo-α-D-quinovopyranosyl)-1-O-behenoyl-propane-1,3-diol sodium salt;
3-O-(6-sulfo-α-D-quinovopyranosyl)-1-O-behenoyl-propane-1,3-diol calcium salt;
3-O-(6-sulfo-α-D-quinovopyranosyl)-1-O-hexanoyl-propane-1,3-diol sodium salt;
3-O-(6-sulfo-α-D-quinovopyranosyl)-1-O-hexanoyl-propane-1,3-diol calcium salt;
3-O-(6-sulfo-α-D-quinovopyranosyl)-1-O-acetyl-propane-1,3-diol sodium salt;
3-O-(6-sulfo-α-D-quinovopyranosyl)-1-O-acetyl-propane-1,3-diol calcium salt;
3-O-(6-sulfo-α-D-quinovopyranosyl)-1-O-formyloxy-propane-1,3-diol sodium salt;
3-O-(6-sulfo-α-D-quinovopyranosyl)-1-O-formyloxy-propane-1,3-diol calcium salt;
3-O-(6-sulfo-β-D-quinovopyranosyl)-1-O-oleoyl-propane-1,3-diol sodium salt;
3-O-(6-sulfo-β-D-quinovopyranosyl)-1-O-oleoyl-propane-1,3-diol calcium salt;
3-O-(6-sulfo-β-D-quinovopyranosyl)-1-O-stearoyl-propane-1,3-diol sodium salt and
3-O-(6-sulfo-β-D-quinovopyranosyl)-1-O-stearoyl-propane-1,3-diol calcium salt.

7. A pharmaceutical composition comprising at least one sulfoquinovosylacyl propanediol compound or pharmaceutically acceptable salt thereof according to claim 1 and a pharmaceutically acceptable carrier.

8. A pharmaceutical composition according to claim 7, which is a radiosensitizer.

9. The pharmaceutical composition according to claim 7, which is an antineoplastic or antitumor agent.

* * * * *

UNITED STATES PATENT AND TRADEMARK OFFICE
CERTIFICATE OF CORRECTION

PATENT NO. : 7,973,145 B2
APPLICATION NO. : 12/322151
DATED : July 5, 2011
INVENTOR(S) : Keisuke Ohta et al.

It is certified that error appears in the above-identified patent and that said Letters Patent is hereby corrected as shown below:

Column 47, Claim 1, Formula (1):

Change:

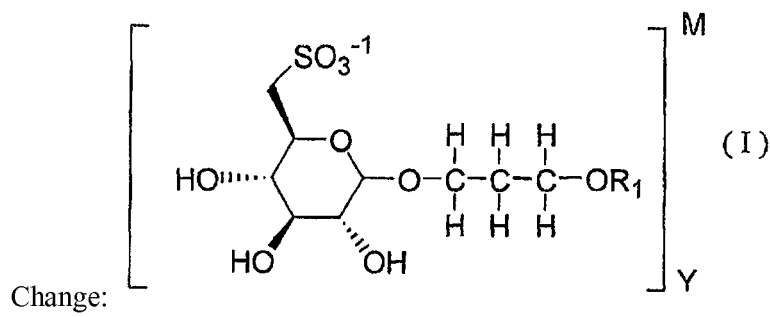

To:

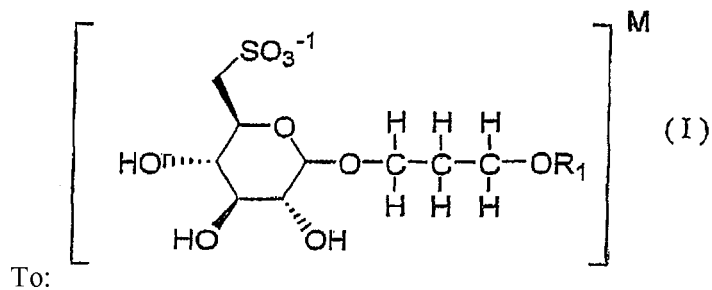

Signed and Sealed this
Twenty-third Day of October, 2012

David J. Kappos
*Director of the United States Patent and Trademark Office*